US012738360B2

(12) United States Patent
Yamamoto et al.

(10) Patent No.: US 12,738,360 B2
(45) Date of Patent: Sep. 15, 2026

(54) DIETARY GUIDANCE SYSTEM, PORTABLE TERMINAL, AND CONTROL METHOD

(71) Applicant: Panasonic Intellectual Property Management Co., Ltd., Osaka (JP)

(72) Inventors: Kohsuke Yamamoto, Osaka (JP); Tomoki Ogawa, Osaka (JP); Shuji Yano, Osaka (JP); Hiroaki Omayu, Osaka (JP)

(73) Assignee: Panasonic Intellectual Property Management Co., Ltd., Osaka (JP)

(*) Notice: Subject to any disclaimer, the term of this patent is extended or adjusted under 35 U.S.C. 154(b) by 138 days.

(21) Appl. No.: 18/577,904

(22) PCT Filed: Jul. 19, 2022

(86) PCT No.: PCT/JP2022/028008
§ 371 (c)(1),
(2) Date: Jan. 9, 2024

(87) PCT Pub. No.: WO2023/002972
PCT Pub. Date: Jan. 26, 2023

(65) Prior Publication Data
US 2024/0321429 A1 Sep. 26, 2024

Related U.S. Application Data

(60) Provisional application No. 63/223,214, filed on Jul. 19, 2021.

(51) Int. Cl.
*G16H 20/60* (2018.01)

(52) U.S. Cl.
CPC .................................. *G16H 20/60* (2018.01)

(58) Field of Classification Search
CPC ..................................................... G16H 20/60
(Continued)

(56) References Cited

U.S. PATENT DOCUMENTS

2010/0240966 A1* 9/2010 Taniike ................. G06Q 99/00
600/301
2017/0242971 A1 8/2017 Kan et al.
(Continued)

FOREIGN PATENT DOCUMENTS

JP 2005-296303 A 10/2005
JP 2016-081519 A 5/2016
JP 2016-103177 A 6/2016

OTHER PUBLICATIONS

International Search Report dated Sep. 27, 2022 issued in International Patent Application No. PCT/JP2022/028008, with English translation.

(Continued)

*Primary Examiner* — Hiep V Nguyen
(74) *Attorney, Agent, or Firm* — RIMON P.C.

(57) ABSTRACT

A dietary guidance system includes an obtainer that obtains a first stage of behavior change defined as a stage of behavior change of a subject of dietary guidance and a second stage of behavior change defined as a stage of behavior change of a food preparer who prepares the subject's meals, and a determiner that determines a course of action for the subject's food based on a third stage of behavior change defined as the lower of the first and second stages of behavior change.

14 Claims, 17 Drawing Sheets

(58) Field of Classification Search
USPC .............................................................. 705/2
See application file for complete search history.

(56) References Cited

U.S. PATENT DOCUMENTS

| | | | | |
|---|---|---|---|---|
| 2018/0256078 | A1* | 9/2018 | Vaterlaus | A61B 5/1118 |
| 2019/0228856 | A1* | 7/2019 | Leifer | G16H 10/60 |
| 2019/0290172 | A1* | 9/2019 | Hadad | A61B 5/14532 |

OTHER PUBLICATIONS

Chiaki Matsumoto, "Model of Behavior Change", The Ministry of Health, Labour and Welfare website, URL: https://www.e-healthnet.mhlw.go.jp/information/exercise/s-07-001.html, Jun. 4, 2019, with its English translation.

* cited by examiner

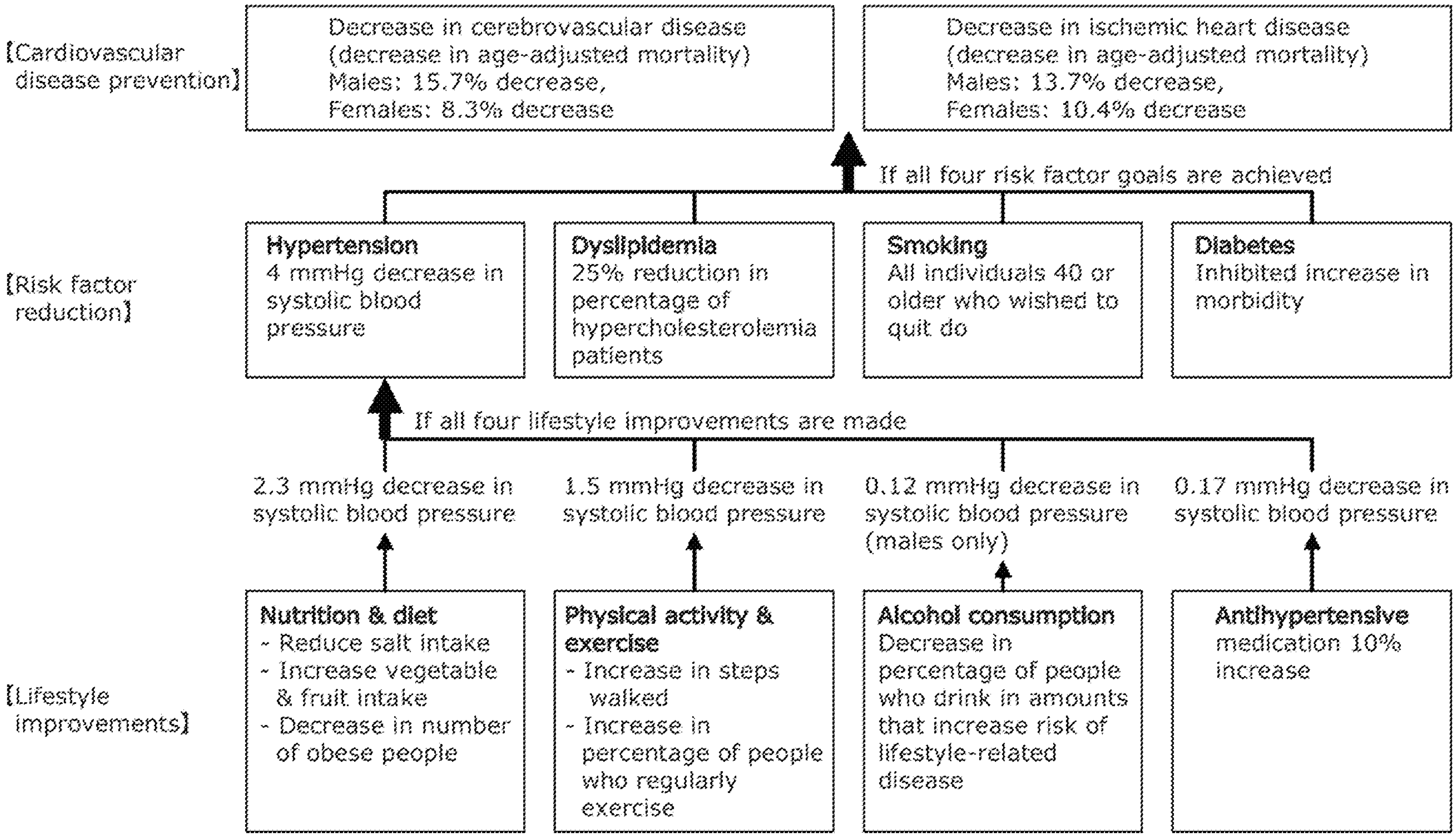

FIG. 4

[Cardiovascular disease prevention]

Decrease in cerebrovascular disease (decrease in age-adjusted mortality) Males: 15.7% decrease, Females: 8.3% decrease Decrease in ischemic heart disease (decrease in age-adjusted mortality) Males: 13.7% decrease, Females: 10.4% decrease If all four risk factor goals are achieved

[Risk factor reduction]

Hypertension 4 mmHg decrease in systolic blood pressure

Dyslipidemia 25% reduction in percentage of hypercholesterolemia patients

Smoking All individuals 40 or older who wished to quit do

Diabetes Inhibited increase in morbidity

If all four lifestyle improvements are made 2.3 mmHg decrease in systolic blood pressure 1.5 mmHg decrease in systolic blood pressure 0.12 mmHg decrease in systolic blood pressure (males only)

0.17 mmHg decrease in systolic blood pressure

[Lifestyle improvements]

Nutrition & diet
- Reduce salt intake
- Increase vegetable & fruit intake
- Decrease in number of obese people

Physical activity & exercise
- Increase in steps walked
- Increase in percentage of people who regularly exercise

Alcohol consumption Decrease in percentage of people who drink in amounts that increase risk of lifestyle-related disease

Antihypertensive medication 10% increase

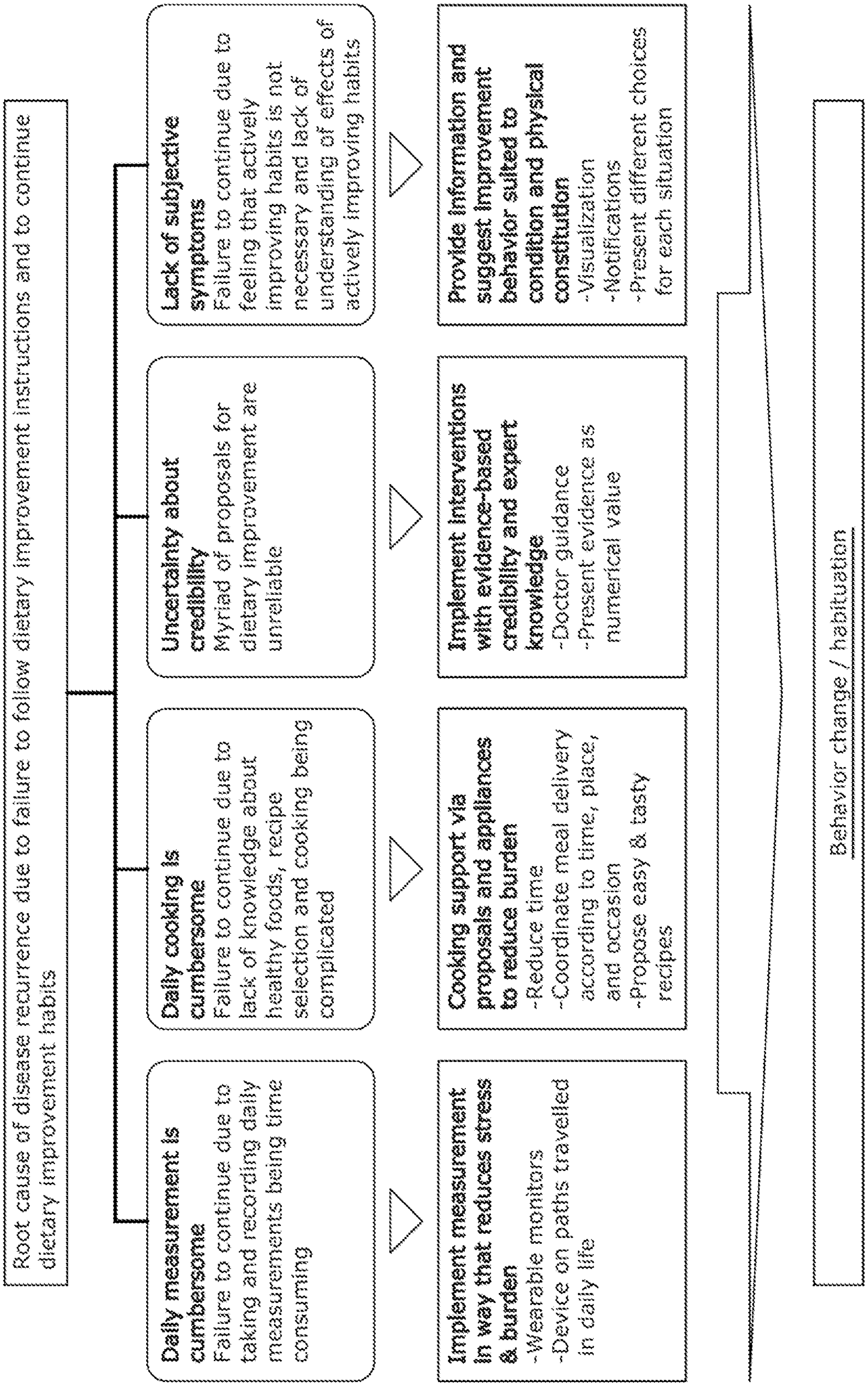

FIG. 5
Root cause of disease recurrence due to failure to follow dietary improvement instructions and to continue dietary improvement habits
Daily measurement is cumbersome
Failure to continue due to taking and recording daily measurements being time consuming
Daily cooking is cumbersome
Failure to continue due to lack of knowledge about healthy foods, recipe selection and cooking being complicated
Uncertainty about credibility
Myriad of proposals for dietary improvement are unreliable
Lack of subjective symptoms
Failure to continue due to feeling that actively improving habits is not necessary and lack of understanding of effects of actively improving habits
Implement measurement in way that reduces stress & burden
-Wearable monitors
-Device on paths travelled in daily life
Cooking support via proposals and appliances to reduce burden
-Reduce time
-Coordinate meal delivery according to time, place, and occasion
-Propose easy & tasty recipes
Implement interventions with evidence-based credibility and expert knowledge
-Doctor guidance
-Present evidence as numerical value
Provide information and suggest improvement behavior suited to condition and physical constitution
-Visualization
-Notifications
-Present different choices for each situation
Behavior change / habituation 10
100
Server
400
300a
Terminal device
300b
Terminal device
300c
Terminal device
201a
Wearable device
202
Healthcare device
203
In-home sensing device
204
Food preparation appliance
201b
Wearable device
Subject
Food preparer
Instructor 300
300
Terminal device
311
Loudspeaker
312
Communicator
313
Touch panel
314
Fingerprint sensor
315
Face recognition sensor
316
Battery
317
Power supply
318
Display
319
Controller
320
Storage
321
GPS
322
Triaxial acceleration sensor
323
Triaxial angular rate sensor
324
Proximity sensor
325
Magnetic sensor
326
Ambient light sensor
327
Microphone
328
Camera
External power source

FIG. 11

| | Subject | Food preparer |
|---|---|---|
| Biometric information | Medical checkup information, electronic medical records, or receipt information, such as blood pressure/vital information, height, weight, age, disease information, blood test data, hospital and medical history, and medication information, exercise habits, sleep state (sleep duration, quality), bowel movements, etc. | |
| Behavior information | Food consumption information (time and content of breakfast, lunch, dinner, snacks, and alcohol consumption), eating out habits, frequency of eating out, food preferences (seasoning, meal content, etc.) occupation, whether a smoker or not, etc. | Shopping frequency, whether or not a meal delivery service, etc., is used, whether or not health foods/supplements are used, time spent on food preparation, appliances and equipment used in food preparation, seasoning preferences, and food preparation methods used during the week (made at home, taking out, eating out, etc.) |
| Goal information | Hobbies, aspired state | Hobbies, aspired state |
| Other information | Evaluation of the meal (i.e., regarding seasoning (light, strong, etc.), quantity (too much, too little, etc.), appearance (balance, color, etc.)) and the food preparation method (ease of preparation, accessibility of ingredients, etc.). | |

FIG. 14

| | First period | Second period | Third period |
|---|---|---|---|
| Content | Prepared edible (group) | Semi-prepared edible (group) | Food preparation method and ingredients for one or more edibles |
| Goal | To get used to the taste | To practice making the food | To prepare food by oneself |
| Stage determination | Contemplation stage | Preparation stage | Action stage |

FIG. 16

| | First or second period | Third period | | |
|---|---|---|---|---|
| Content | Prepared edible (group) or semi-prepared edible (group) | Present food preparation or eating method that focuses on serving (e.g., reduce amount of soup to half, reduce frequency of fried foods, increase dishes with fish with a bluish back) | Present salt-free or low-salt alternatives to familiar foods | Food preparation method and ingredients for one or more edibles |
| Goal | To get used to the taste or learn how to make the food | To prepare food by oneself | | |
| Stage determination | Contemplation stage | Preparation stage (early on) | Preparation stage (later on) | Action stage |

FIG. 17

| | First or second period | Third period |
|---|---|---|
| Content | Prepared edible (group) or semi-prepared edible (group) | Food preparation method and ingredients for one or more edibles |
| Goal | To get used to the taste or learn how to make the food | To prepare food by oneself |
| Stage determination | Contemplation stage | Preparation stage |

DIETARY GUIDANCE SYSTEM, PORTABLE TERMINAL, AND CONTROL METHOD

CROSS-REFERENCE OF RELATED APPLICATIONS

This application is the U.S. National Phase under 35 U.S.C. § 371 of International Patent Application No. PCT/JP2022/028008, filed on Jul. 19, 2022, which in turn claims the benefit of U.S. Provisional Patent Application No. 63/223,214, filed on Jul. 19, 2021, the entire disclosures of which applications are incorporated by reference herein.

TECHNICAL FIELD

The present disclosure relates to a dietary guidance system, a terminal device, and a control method.

BACKGROUND ART

PTL 1 discloses a technique for evaluating a subject's psychological characteristics with respect to the subject's targeted biological or behavior change. PTL 2 discloses a technique for instructing human behavior change and habitualization. PTL 3 discloses a technique for optimizing dietary guidance content according to a user's preferences and state of behavior change.

CITATION LIST

Patent Literature

[PTL 1] Japanese Unexamined Patent Application Publication No. 2016-81519
[PTL 2] Japanese Unexamined Patent Application Publication No. 2005-296303
[PTL 3] Japanese Unexamined Patent Application Publication No. 2016-103177

SUMMARY OF INVENTION

Technical Problem

The present disclosure provides a dietary guidance system, etc., that can effectively provide dietary guidance.

Solution to Problem

A dietary guidance system according to one aspect of the present disclosure includes: an obtainer that obtains a first stage of behavior change defined as a stage of behavior change of a subject of dietary guidance and a second stage of behavior change defined as a stage of behavior change of a food preparer who prepares food for the subject; and a determiner that determines a course of action related to the food for the subject based on a third stage of behavior change defined as a lower one of the first stage of behavior change or the second stage of behavior change.

A terminal device according to one aspect of the present disclosure includes: an obtainer that obtains information indicating a course of action that is related to food for a subject of dietary guidance and determined based on a third stage of behavior change defined as a lower one of a first stage of behavior change defined as a stage of behavior change of the subject or a second stage of behavior change defined as a stage of behavior change of a food preparer who prepares food for the subject; and a presenter that presents the course of action to the subject or the food preparer.

These general or specific aspects may be implemented as a device/apparatus, a method, an integrated circuit, a computer program, or a computer-readable recording medium such as a CD-ROM, or any combination thereof.

Advantageous Effects of Invention

The present disclosure can provide a dietary guidance system, etc., that can effectively provide dietary guidance.

BRIEF DESCRIPTION OF DRAWINGS

FIG. 4 illustrates factors that reduce blood pressure.

FIG. 5 illustrates factors that prevent people from continuing to improve their lifestyle habits.

FIG. 11 illustrates examples of the biometric information, behavior information, goal information, and other information according to an embodiment.

FIG. 14 illustrates an example of courses of action according to an embodiment.

FIG. 16 illustrates a variation of courses of action according to an embodiment.

FIG. 17 illustrates a variation of courses of action according to an embodiment.

DESCRIPTION OF EMBODIMENTS

Background

The background of the invention will be explained.

Figure 1:
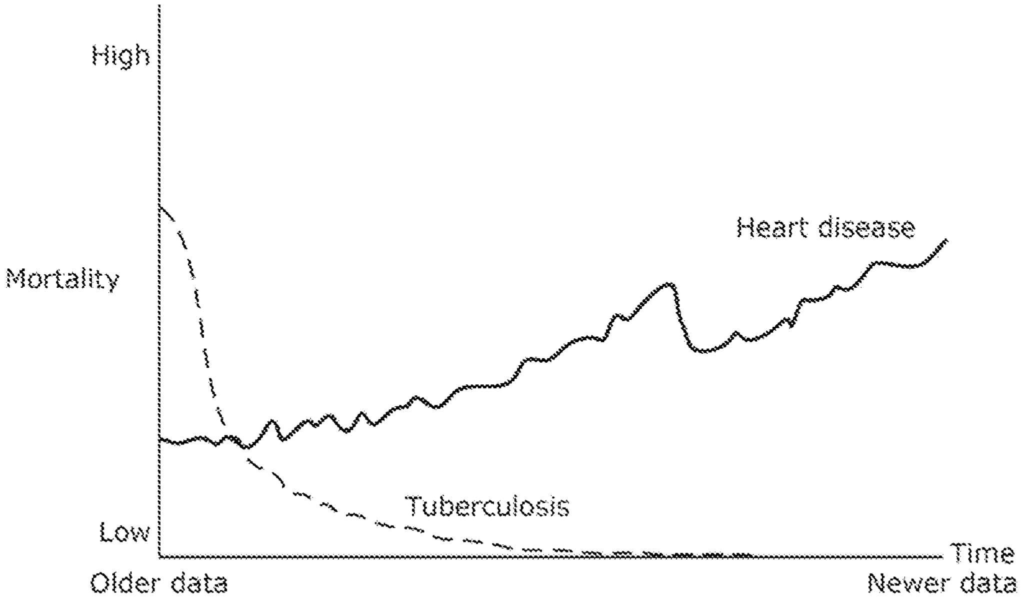
FIG. 1 is a graph for illustrating changes in disease structure.

FIG. 1 is a graph for illustrating changes in disease structure.

As illustrated in FIG. 1, the structure of diseases affecting the Japanese population has shifted from infectious diseases to lifestyle-related diseases as sanitary conditions improved in the postwar period. For example, mortality from infectious diseases such as tuberculosis and pneumonia has been decreasing over time, while mortality from lifestyle-related diseases such as heart disease has been increasing. Lifestyle-related diseases are difficult to cure, so the cost of treatment is an ongoing problem. Additionally, in lifestyle-related diseases, the intensity of the patient's subjective symptoms does not correspond to the necessity of medical intervention.

Figure 2:
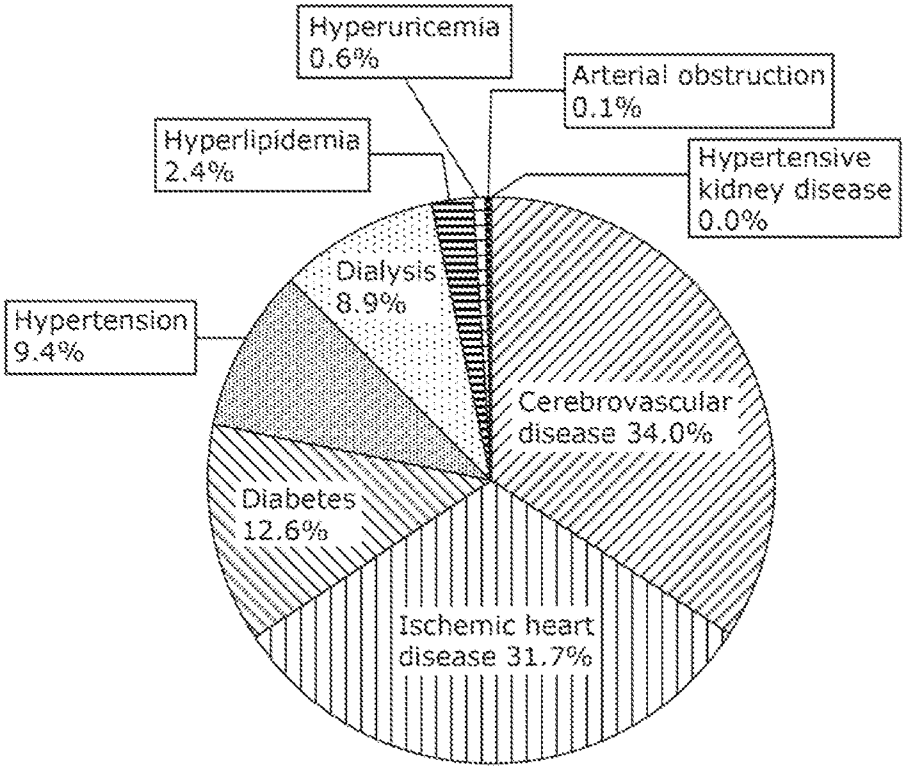
FIG. 2 is a graph illustrating percentages of medical expenditures for different lifestyle-related diseases.
Figure 3:
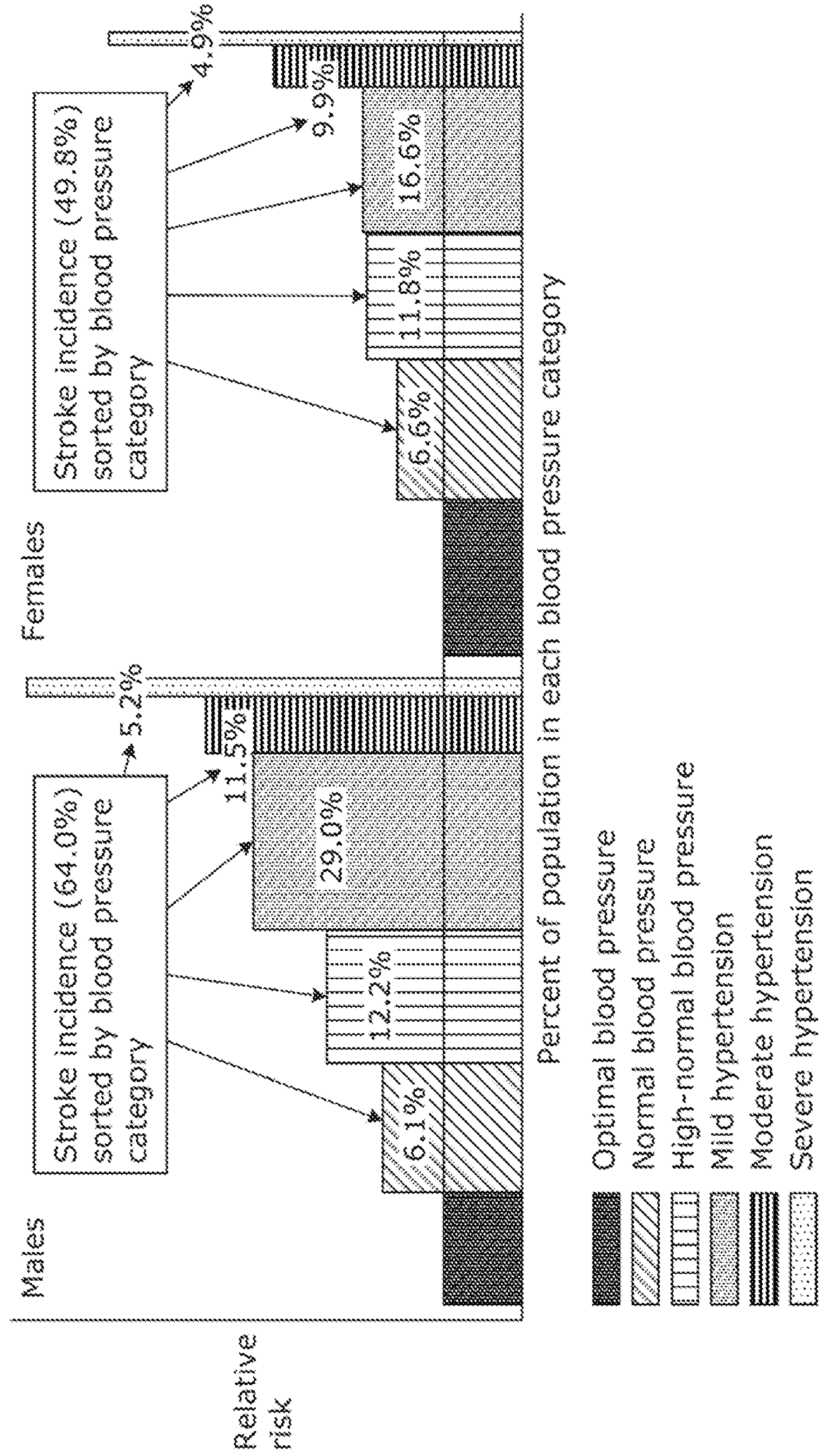
FIG. 3 is a graph illustrating the relationship between blood pressure categories and stroke incidence.

FIG. 2 is a graph illustrating percentages of medical expenditures for different lifestyle-related diseases. FIG. 3 is a graph illustrating the relationship between blood pressure categories and stroke incidence.

As illustrated in FIG. 2, about 75% of the medical expenditures for lifestyle-related diseases are spent on diseases in which high blood pressure is the main cause (cerebrovascular disease, ischemic heart disease, and hypertension). Multiple studies have also found that the risk of disease increases with higher blood pressure. For example, as illustrated in FIG. 3, the risk of stroke increases with higher blood pressure.

FIG. 4 illustrates factors that reduce blood pressure. FIG. 4 is a diagram based on the Guidelines for the Management of Hypertension 2019.

As illustrated in FIG. 4, four measures are considered important to reduce blood pressure: (1) nutrition and diet, (2) physical activity and exercise, (3) alcohol consumption, and (4) antihypertensive medication rates. Of these, (1) nutrition and diet, (2) physical activity and exercise, and (3) alcohol consumption are not medical measures, but measures related to improving one's everyday lifestyle. In other words, improving one's everyday lifestyle is important for reducing lifestyle-related diseases.

FIG. 5 illustrates factors that prevent people from continuing to improve their lifestyle habits.

In order to improve lifestyle habits in patients with lifestyle-related diseases, it is necessary to habituate behaviors that lead to good health on a patient by patient basis. If a person is able to habituate behaviors that lead to good health, it will help promote and maintain their health.

However, it is difficult to sustain lifestyle improvement behavior without following lifestyle (for example, diet) improvement instructions. Four conceivable factors for this difficulty are, for example, (1) daily measurement is cumbersome, (2) daily cooking is cumbersome, (3) uncertainty about the credibility of the information, and (4) lack of subjective symptoms. The four factors can be improved to habituate lifestyle improvement behaviors (behavior change). For example, (1) could be improved by implementing measurement in a way that reduces stress and burden. For example, (2) could be improved by implementing meal proposals that reduce the burden of cooking and implementing cooking support via home appliances. For example, (3) could be improved by implementing interventions with evidence-based credibility and expert knowledge. For example, (4) could be improved by providing information and suggesting improvement behavior suited to the condition and physical constitution of the individual.

Figure 6:
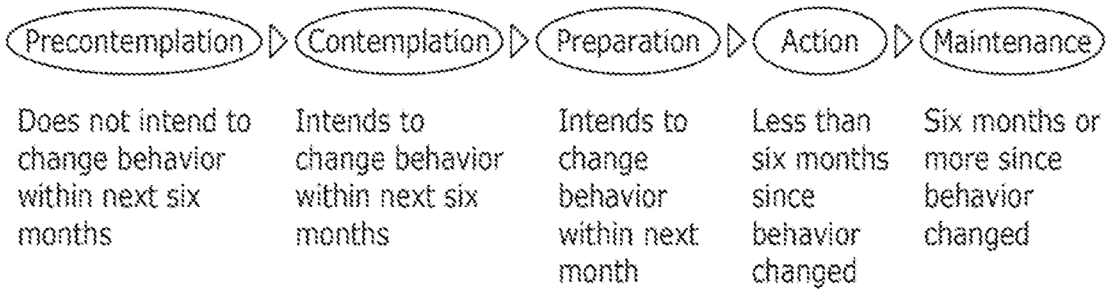
FIG. 6 is a diagram illustrating a model of behavior change.

FIG. 6 is a diagram illustrating a model of behavior change.

It is common for individuals to change their behavior in gradual stages. As illustrated in FIG. 6, individuals are considered to progress through five stages of behavior change: precontemplation, contemplation, preparation, action, and maintenance. These five stages make up the model of behavior change, which is being researched and practiced on various health-related behaviors. In order to advance even one stage of behavior change, it is first necessary to know which stage the individual is in and to work with them according to the stage. The stages of behavior change are evaluated from low to high in the order of precontemplation, contemplation, preparation, action, and maintenance. In other words, the stages of behavior change of precontemplation, contemplation, preparation, action, and maintenance are listed in ascending order in terms of their evaluation, such that the contemplation stage is evaluated higher than the precontemplation stage, the preparation stage is evaluated higher than the contemplation stage, the action stage is evaluated higher than the preparation stage, and the maintenance stage is evaluated higher than the action stage. Thus, an individual's stage of behavior change can be said to be an indicator of their degree of willingness to change their daily behavior to transition from a first state to a second, improved state.

For example, the Ministry of Health, Labour and Welfare website (https://www.e-healthnet.mhlw.go.jp/information/exercise/s-07-001.html) discloses a model of behavior change and stage-appropriate approaches, which are described below.

Approaches for the precontemplation stage include, for example, raising awareness, learning about the benefits of physical activity, emotional experiences, realizing that the status quo needs to change, re-evaluating one's environment, and realizing how one's behavior impacts their surroundings.

Approaches for the contemplation stage include, for example, re-evaluation of oneself, and presenting physical inactivity as harmful and physical activity as beneficial.

Approaches for the preparation stage include, for example, personal determination and having confidence in one's ability to perform physical activity well and declaring to others that one is ready to begin physical activity.

Approaches for the action and maintenance stages include, for example, behavior replacement, replacing unhealthy behaviors with healthy ones (for example, using physical activity instead of alcohol to cope with stress), supportive relationships, using the support of others to continue physical activity, reinforcement management, giving 'rewards' for continuing physical activity, stimulus control, and creating an environment conducive to physical activity.

(Blood Pressure Monitor)

In recent years, wearable cuffless blood pressure monitors have been developed to automatically measure blood pressure at regular intervals. Cuffless blood pressure monitors are approved as medical devices in some countries or regions.

Unlike conventional blood pressure monitors, cuffless blood pressure monitors are devices that are worn, for example, on the wrist or upper arm, and enable frequent and automatic blood pressure measurements at predetermined times without the user noticing, such as at 30-minute intervals, or when predetermined conditions are met (for example, when the user is at rest and there is little movement).

Conventionally, a blood pressure monitor with a cuff called Ambulatory Blood Pressure Monitoring (ABPM) has been used to obtain frequent blood pressure readings (for example, hourly blood pressure readings), but the periodic tightening of the cuff places stress on the subject's body. For this reason, frequent blood pressure values are rarely measured except in medical facilities when truly needed.

On the other hand, rather than using a cuff, cuffless blood pressure monitors obtain blood pressure readings by estimating blood pressure based on, for example, pulse waves obtained from an optical sensor, with little or no tightening of the body measurement position (wrist, upper arm, etc.). Thus, blood pressure can be measured frequently without placing stress on the subject's body as with ABPM.

(Smartphone Apps for Supporting Improvement Behavior)

In recent years, health management apps have been developed that keep a record of the user's physical condition, such as keeping a food consumption log (content of daily meals), an exercise log (content of daily exercise), and a weight log, to visualize the user's health condition for dieting purposes. In such a health management app, for example, data recorded daily, such as a food consumption log, an exercise log, and physical condition, is checked by a nutritionist, and advice from the nutritionist is provided according to the user's diet goals. This allows the user to follow the advice of their nutritionist to improve their eating habits and exercise routines. Moreover, the app allows the user to browse a large number of cooking recipes and cook using recipes that follow the advice of their nutritionist.

In addition to manual input by the user, meal contents may be input in this app by citing cooking recipes in the app or by taking a photo of the meal and having the AI in the app predict the meal contents from the photo and using the prediction results. Moreover, meal contents may be input in this app by searching for store names and product names and selecting store names and product names if they are affiliated with the app. Reducing the time and complexity of entering meal contents is known to encourage continued use of the app.

(Problem)

To improve hypertension or some other disease, when a user who receives support for lifestyle improvement (hereinafter "supported user") and a user who supports the lifestyle improvement of the supported user (hereinafter "supporting user") work together to improve the lifestyle (for example, eating habits) of the supported user, the following problems must be addressed. Here, the supported user and the supporting user are partners, such as a married couple. For example, if the supported user and the supporting user are in different stages of behavior change, trouble may occur between the supported user and the supporting user, and the supported user may not be able to make good progress in their efforts to improve their lifestyle and consequently may not engage in lifestyle improvement behavior. Note that a supported user refers to a user (patient) who has a disease such as hypertension and needs to improve their lifestyle in order to improve the disease, and a supporting user refers to a user who helps the supported user improve their lifestyle, for example, by cooking the supported user's meals.

The inventors found that this problem is based on, for example, the relationship between and the magnitudes of the stages of behavior change, as shown below.

(1) When the Supported User's Stage of Behavior Change is Higher than the Supporting User's Stage of Behavior Change The supported user may not be conscious of improving their lifestyle and may not listen to the supporting user's recommendations to eat a low-sodium diet, making it difficult for both parties to discuss improvement behaviors. As a result, the supporting user loses motivation to support the supported user in improving their lifestyle.

Even if the supporting user prepares and serves a low-sodium meal, the supported user may have a preconceived notion that the meal will not taste good before eating it, and will not want to eat it. The supporting user loses motivation to support the supported user in improving their lifestyle when the supported user does not eat the low-sodium meal they cooked for them.

Even if the supporting user prepares a low-sodium meal, the supported user may complain that the meal does not taste good and will not eat much. The supporting user may also gradually lose motivation if the supported user does not make an effort to improve their lifestyle.

Even if the supporting user prepares a low-sodium meal, the supported user may be not satisfied and eat a heavily seasoned meal when the supporting user is not around (for example, by eating out). The supporting user loses motivation to support the supported user when they find out that the supported user is eating as they please behind their back.

(2) When the Supported User's Stage of Behavior Change is Lower than the Supporting User's Stage of Behavior Change The supporting user does may not have the awareness to cook a low-sodium meal for the supported user, so the supported user performs the improvement behavior alone.

The supporting user may have a preconceived notion that low-sodium food does not taste good and may not cook low-sodium meals. As a result, the supported user may have no choice but to improve their diet outside of the home, limiting their means of improvement.

Suppose the supporting user wants to cook a low-sodium meal, but low-sodium meals often include fish dishes, which require the supporting user to be highly skilled at cooking.

Even if the supporting user initially cooperates and prepares low-sodium meals, the supporting user may not want to continue eating them themselves, so they may stop preparing low-sodium meals. As a result, the supported user may have no choice but to improve their diet outside of the home, limiting their means of improvement.

(3) When the Supported User and the Supporting User are at the Same Stage of Behavior The supported user and the supporting user may both have a preconceived notion that low-sodium meals do not taste good before eating them, and will not want to eat them. As a result, the stage of behavior change of the supported user is not raised and health improvement does not progress.

Even if the supported user and the supporting user prepare a low-sodium meal, they may complain that the meal does not taste good and not eat much. As a result, both the supported user and the supporting user will start to prepare low-sodium meals less frequently, impeding progression of their health improvement.

In order to overcome the above problems, the present inventors have discovered a dietary guidance system that can effectively provide dietary guidance.

A dietary guidance system according to one aspect of the present disclosure includes: an obtainer that obtains a first stage of behavior change defined as a stage of behavior change of a subject of dietary guidance and a second stage of behavior change defined as a stage of behavior change of a food preparer who prepares food for the subject; and a determiner that determines a course of action related to the food for the subject based on a third stage of behavior change defined as a lower one of the first stage of behavior change or the second stage of behavior change.

With this, a course of action related to the food for the subject is determined based on a third stage of behavior change defined as a lower one of the first stage of behavior change or the second stage of behavior change. Accordingly, by using a course of action suited to the individual at the lower stage of behavior change, it is possible to inhibit a decline in motivation of the individual at the lower stage of behavior change and effectively raise their stage of behavior change. This allows the dietary guidance system to effectively provide dietary guidance.

For example, when the third stage of behavior change is a first stage, the determiner may determine, as the course of action, a first course of action related to preparing the food for the subject, and when the third stage of behavior change is a second stage higher than the first stage, the determiner may determine, as the course of action, a second course of action related to preparing the food for the subject. The first course of action may require less preparation by the food preparer than the second course of action.

With this, the dietary guidance system can provide a course of action suited to the stage of behavior change. In low stages of behavior change in particular, the food preparer's effort can be reduced, thus maintaining or increasing the food preparer's motivation to continue dietary guidance.

For example, when the third stage of behavior change is a third stage higher than the second stage, the determiner may determine, as the course of action, a third course of action related to preparing the food for the subject. The third course of action may require more preparation by the food preparer than the second course of action.

With this, the dietary guidance system can provide a course of action suited to the stage of behavior change. In particular, by the food preparer's effort increasing gradually, the food preparer's motivation to continue dietary guidance can be maintained or increased.

For example, the first course of action may be providing the subject and the food preparer with prepared food. The second course of action may be providing the food preparer with a partially prepared ingredient and having the food preparer carry out partial food preparation. The third course of action may be providing the food preparer with an unprepared ingredient and having the food preparer carry out food preparation.

With this, the dietary guidance system can provide a course of action suited to the stage of behavior change.

For example, the partially prepared ingredient may include pre-measured seasoning.

With this, the dietary guidance system can effectively reduce the food preparer's effort.

For example, the same food may be provided to the subject in the first course of action and the second course of action.

With this, the dietary guidance system allows the subject to try out and get used to foods at a lower stage which requires less food preparation. It is therefore possible to inhibit the occurrence of food that is not to the subject's taste, etc., after much effort has been taken to prepare it, thereby maintaining or improving the food preparer's and the subject's motivation to continue their dietary guidance.

For example, the obtainer may obtain the first stage of behavior change and the second stage of behavior change by determining the first stage of behavior change based on at least one of behavior information, biometric information, or goal information of the subject and determining the second stage of behavior change based on at least one of behavior information or goal information of the food preparer. The obtainer may update the first stage of behavior change and the second stage of behavior change upon each elapse of a predetermined number of days. The determiner may update the course of action upon each elapse of the predetermined number of days.

With this, the dietary guidance system can regularly update the stage of behavior change and the course of action.

For example, on condition of confirmation of the subject exhibiting a predetermined behavior based on the behavior information, (i) the obtainer may the first stage of behavior change and the second stage of behavior change regardless of the elapse of the predetermined number of days and (ii) the determiner may update the course of action regardless of the elapse of the predetermined number of days.

With this, the dietary guidance system can promptly provide feedback to the subject and the food preparer, for example, when it detects a predetermined behavior that affects the subject's physical condition, etc. This makes it possible to inhibit the subject from exhibiting a predetermined behavior, and quickly determine an appropriate course of action.

For example, the predetermined behavior may include high salt intake.

A terminal device according to one aspect of the present disclosure includes: an obtainer that obtains information indicating a course of action that is related to food for a subject of dietary guidance and determined based on a third stage of behavior change defined as a lower one of a first stage of behavior change defined as a stage of behavior change of the subject or a second stage of behavior change defined as a stage of behavior change of a food preparer who prepares food for the subject; and a presenter that presents the course of action to the subject or the food preparer.

With this, a course of action related to the food for the subject is determined based on a third stage of behavior change defined as a lower one of the first stage of behavior change or the second stage of behavior change. Accordingly, by using a course of action suited to the individual at the lower stage of behavior change, it is possible to inhibit a decline in motivation of the individual at the lower stage of behavior change and effectively raise their stage of behavior change. This allows the dietary guidance system that uses the terminal device to effectively provide dietary guidance.

A control method according to one aspect of the present disclosure is a control method of a dietary guidance system including one or more processors, and includes, executed by the one or more processors: obtaining a first stage of behavior change defined as a stage of behavior change of a subject of dietary guidance and a second stage of behavior change defined as a stage of behavior change of a food preparer who prepares food for the subject; and determining a course of action related to the food for the subject based on a third stage of behavior change defined as a lower one of the first stage of behavior change or the second stage of behavior change.

With this, a course of action related to the food for the subject is determined based on a third stage of behavior change defined as a lower one of the first stage of behavior change or the second stage of behavior change. Accordingly, by using a course of action suited to the individual at the lower stage of behavior change, it is possible to inhibit a decline in motivation of the individual at the lower stage of behavior change and effectively raise their stage of behavior change. This allows the dietary guidance system that uses the control method to effectively provide dietary guidance.

A control method according to one aspect of the present disclosure is a control method of a dietary guidance system including one or more processors, and includes, executed by the one or more processors: obtaining a course of action that is related to food for a subject of dietary guidance and determined based on a third stage of behavior change defined as a lower one of a first stage of behavior change defined as a stage of behavior change of the subject or a second stage of behavior change defined as a stage of behavior change of a food preparer who prepares food for the subject; and presenting information about the course of action to the subject or the food preparer.

With this, a course of action related to the food for the subject is determined based on a third stage of behavior change defined as a lower one of the first stage of behavior change or the second stage of behavior change. Accordingly, by using a course of action suited to the individual at the lower stage of behavior change, it is possible to inhibit a decline in motivation of the individual at the lower stage of behavior change and effectively raise their stage of behavior change. This allows the dietary guidance system that uses the control method to effectively provide dietary guidance.

For example, a program according to one aspect of the present disclosure is a program for causing a computer to execute the control method.

These general or specific aspects may be implemented as a device/apparatus, a method, an integrated circuit, a computer program, or a computer-readable recording medium such as a CD-ROM, or any combination thereof.

Hereinafter, embodiments will be described in detail with reference to the drawings, but unnecessarily detailed descriptions may be omitted. For example, detailed descriptions of well-known matters or descriptions of elements that are substantially the same as previously described elements may be omitted. This is to avoid redundancy and provide easily read descriptions for those skilled in the art.

Note that the inventors have provided the appended drawings and following description for the purpose of facilitating sufficient understanding of the present disclosure by those skilled in the art. Accordingly, the appended drawings and following description are not intended to limit the scope of the claims.

EMBODIMENT

[Configuration]

Figure 7:
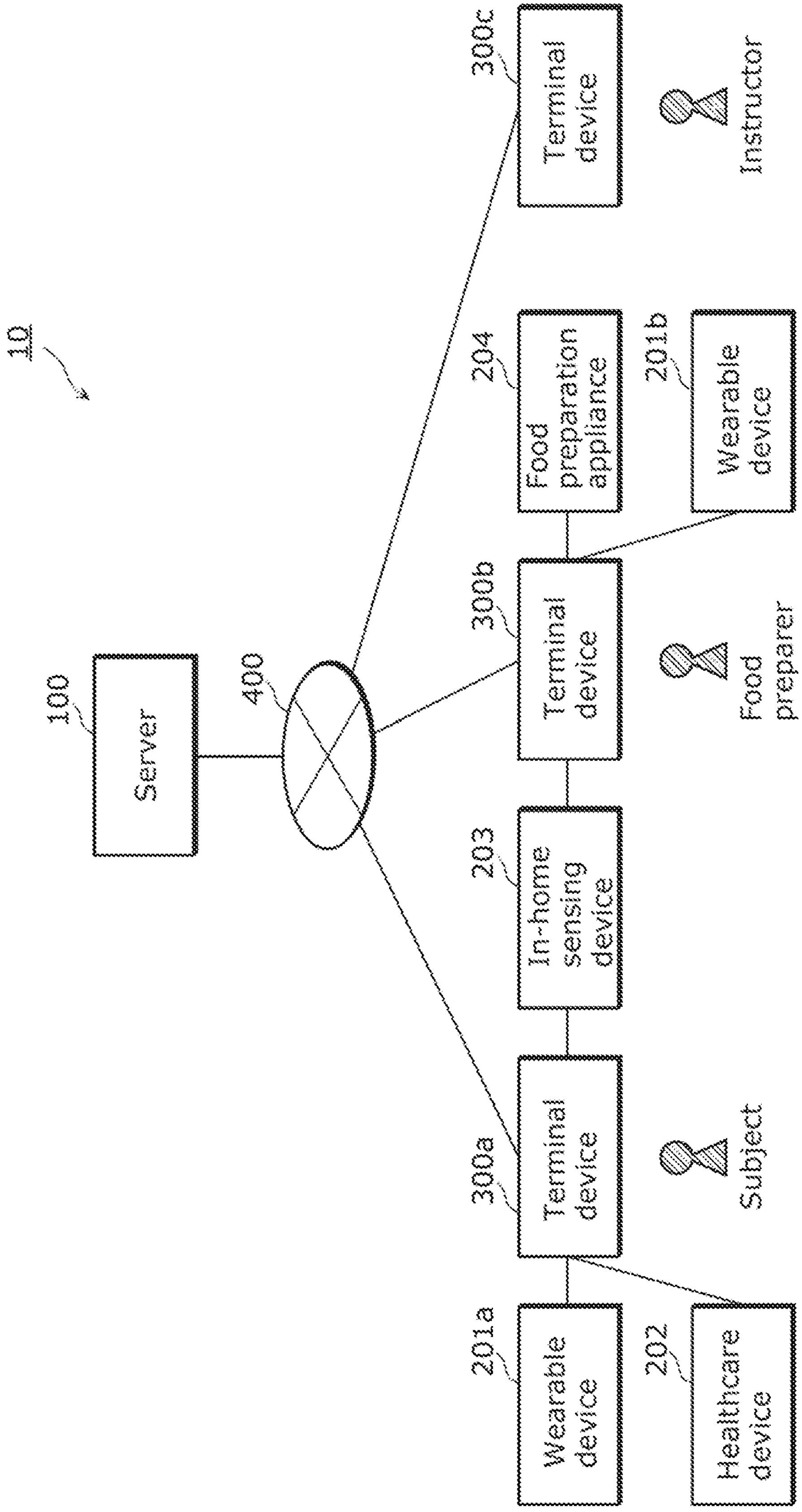
FIG. 7 illustrates an example of the configuration of a dietary guidance system according to an embodiment.

FIG. 7 illustrates an example of the configuration of dietary guidance system 10 according to the present embodiment. Dietary guidance system 10 is a system for providing dietary guidance to a subject. The subject is a person who will receive support for lifestyle improvement, and corresponds to the supported user described above. The food preparer is a person who prepares the subject's food, and corresponds to the supporting user who supports the lifestyle improvement of the supported user. For example, the subject and the food preparer are partners, such as a married couple. For example, the subject is a hypertensive patient, and courses of action related to the subject's food (for example, involving low-sodium dishes) are provided as dietary guidance.

As illustrated in FIG. 7, dietary guidance system 10 includes server 100, wearable devices 201*a* and 201*b*, healthcare device 202, in-home sensing device 203, food preparation appliance 204, and terminal devices 300*a*, 300*b*, and 300*c*.

Terminal devices 300*a*, 300*b*, and 300*c* are terminals used by the subject, food preparer, and instructor, respectively. Here, the instructor is, for example, a physician, dietitian, or public health nurse who provides health guidance such as reducing salt intake to the subject and the food preparer. In the following description, the term "terminal device 300" may be used when there is no need to specifically distinguish between terminal devices 300*a*, 300*b*, and 300*c*, with the understanding that the description applies to each of terminal devices 300*a*, 300*b*, and 300*c*.

Terminal device 300 may be, but is not limited to, a portable terminal (for example, a smartphone, a tablet terminal, a laptop Personal Computer (PC), etc.), a desktop PC, etc. Terminal device 300 is connected to other devices via a network such as a Wireless Local Area Network (WLAN) or using short-range wireless communication such as Bluetooth, and can exchange data with the devices to which it is connected.

More specifically, the subject's terminal device 300*a* is connected to wearable device 201*a* and healthcare device 202 used by the subject, and in-home sensing device 203. For example, terminal device 300*a* receives the subject's biometric information from healthcare device 202 and receives the subject's behavior information from wearable device 201*a* and in-home sensing device 203.

Healthcare device 202 is, for example, a blood pressure monitor, a scale, a blood glucose meter, a pedometer, or an activity meter. Wearable devices 201*a* and 201*b* are, for example, smart watches or other wearable devices.

Terminal device 300*a* is connected to server 100 via network 400. Network 400 may be a general-purpose line, such as the Internet, or a dedicated line. Terminal device 300*a* and server 100 can exchange data with each other. The subject's biometric information and behavior information is transmitted to server 100 from healthcare device 202, wearable device 201*a*, and in-home sensing device 203 via terminal device 300*a*.

Terminal device 300*b* is connected to server 100 via network 400. Terminal device 300*b* and server 100 can exchange data with each other. The food preparer's behavior information is transmitted to server 100 from wearable device 201*b*, in-home sensing device 203, and food preparation appliance 204 via terminal device 300*b*.

In-home sensing device 203 is, for example, a thermometer, a camera, a pulse wave measurement device, a heart rate measurement device, an activity measurement device, a behavior measurement device, or an environmental data measurement device.

Server 100 may be a single server or may include a plurality of servers. For example, server 100 may include some or all of a server that provides communication functions and a Personal Health Record (PHR) server.

The behavior information of the subject and the food preparer is obtained, for example, from at least one of terminal device 300*a*, terminal device 300*b*, wearable device 201*a*, wearable device 201*b*, in-home sensing device 203, or food preparation appliance 204. For example, the behavior information includes a food consumption log or shopping frequency, which are managed by an application installed on these devices that obtain a meal suggestion or meal information. The behavior information may include preparation time or information from equipment or an appliance used in the food preparation, obtained from food preparation appliance 204.

The behavior information may include information obtained from the instructor's terminal device 300*c*. Goal information is, for example, information obtained by an application that operates on terminal devices 300*a* and 300*b*. Alternatively, goal information is information obtained through interviews based on a questionnaire or otherwise with the subject and the food preparer conducted by a physician, dietitian, or nutrition guidance service.

The configuration illustrated in FIG. 7 is merely one example; not all of these devices need necessarily be included in dietary guidance system 10. For example, if terminal device 300*a* has the function of obtaining the subject's biometric information and behavior information, such as when terminal device 300*a* includes, for example, a biometric sensor and a motion sensor, wearable device 201*a* and healthcare device 202, etc., are not necessary. Moreover, the connectivity between the devices illustrated in FIG. 7 is merely one example; the devices may be arbitrarily connected. For example, in the example illustrated in FIG. 7, wearable devices 201*a* and 201*b*, healthcare device 202, in-home sensing device 203, and food preparation appliance

204 are connected to server 100 via terminal device 300*a* or 300*b*, but at least one of these devices may be connected to server 100 or network 400 without going through terminal device 300*a* or 300*b*. For example, at least one of these devices may be connected to server 100 or network 400 via some other device such as a router.

(Specific Example of Terminal Device)

Figure 8:
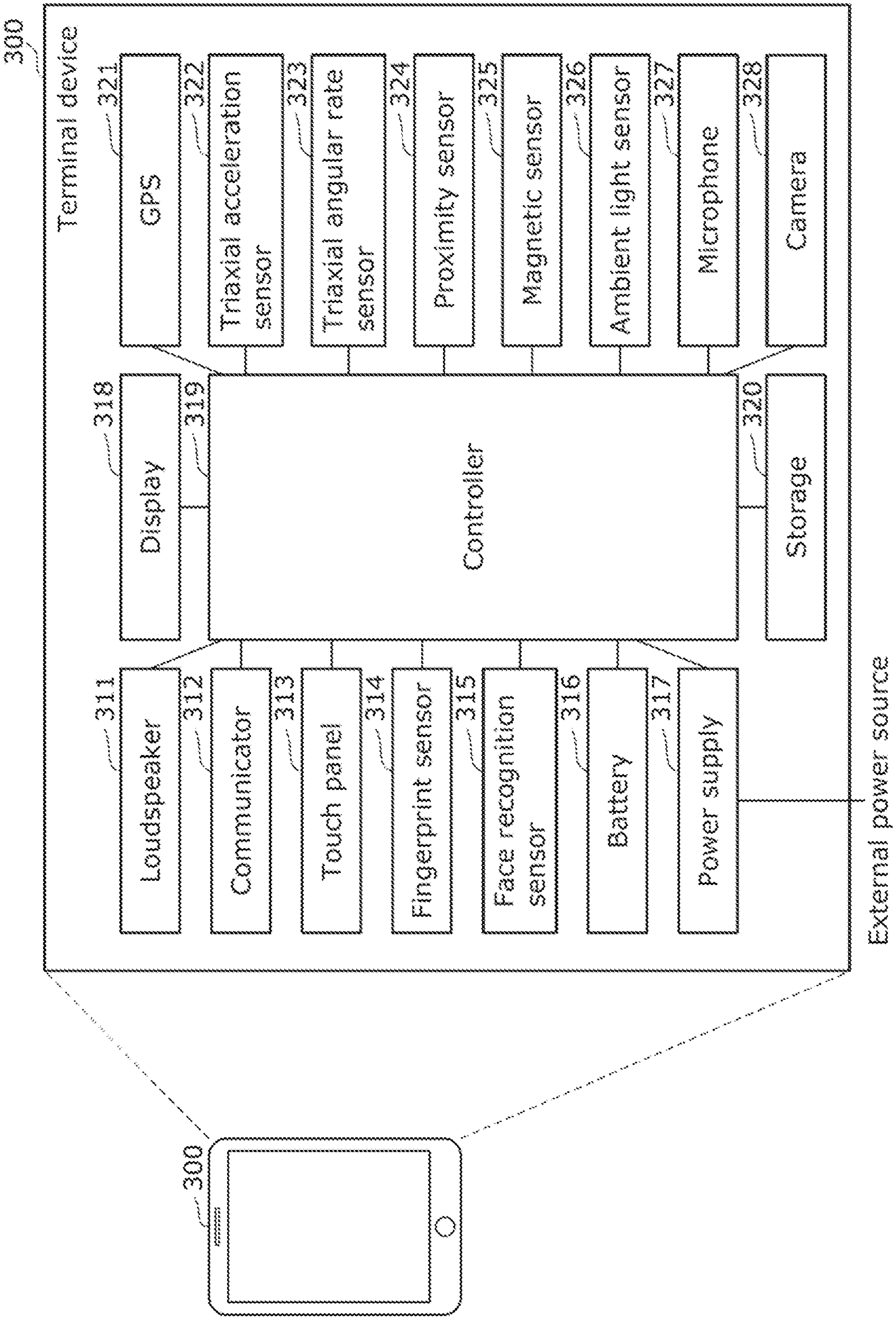
FIG. 8 illustrates the configuration of a terminal device according to an embodiment in detail.

FIG. 8 illustrates the configuration of terminal device 300 in detail. FIG. 8 schematically illustrates the block configuration of a smartphone as one example of terminal device 300.

As illustrated in FIG. 8, terminal device 300 includes loudspeaker 311, communicator 312, touch panel 313, fingerprint sensor 314, face recognition sensor 315, battery 316, power supply 317, display 318, controller 319, storage 320, GPS 321, triaxial acceleration sensor 322, triaxial angular rate sensor 323, proximity sensor 324, magnetic sensor 325, ambient light sensor 326, microphone 327, and camera 328.

Controller 319 is capable of integrally controlling terminal device 300 and includes a central processing unit (CPU) and a memory element (such as SRAM) (not illustrated). Display 318 is a display that displays text and graphics based on information received from controller 319. Storage 320 stores the operating system (OS) to be read and executed by controller 319, various application programs (generally referred to as smartphone apps), and various data used by various programs. Storage 320 includes a nonvolatile storage area.

Communicator 312 implements wireless communication functions such as long term evolution (LTE) and 5G, and is wirelessly connected to a base station of a cellular phone communication network (not illustrated) and connected to the internet via the base station. Communicator 312 may implement wireless communication functions via Bluetooth (registered trademark) or wireless LAN (for example, Wi-Fi (registered trademark)). Communicator 312 may be connected to the internet via Bluetooth or wireless LAN (for example, Wi-Fi) through other communication devices.

Touch panel 313 accepts input from the user to the UI displayed on display 318 and transmits signals based on the input (for example, which part of the screen is being touched and with what degree of pressure) to controller 319. GPS 321 measures the geographical position of terminal device 300. Triaxial acceleration sensor 322 sets the X-, Y-, and Z-axes for terminal device 300, and measures acceleration in each axis. Triaxial angular rate sensor 323 measures angular velocity in the direction of rotation for each axis. Proximity sensor 324 detects objects in close proximity (for example, a face approaching the smartphone). Magnetic sensor 325 detects the geomagnetic field and indicates the direction. Ambient light sensor 326 detects the ambient brightness of terminal device 300. Microphone 327 collects ambient sounds and speech. Camera 328 captures images from the front of terminal device 300, where display 318 is located, or from the rear on the opposite side. Loudspeaker 311 emits sound based on audio signals generated by controller 319. Fingerprint sensor 314 is used for user authentication, etc., and detects a person's fingerprint. Face recognition sensor 315 authenticates a person's face. Face recognition sensor 315 may be realized by combining an infrared camera, a projection illuminator, a dot projector, etc., with a group of sensors (a proximity sensor, a camera, and an ambient light sensor).

Power supply 317 receives a supply of power from an external power source. Battery 316 stores the external power received by power supply 317 or supplies the stored power to terminal device 300 for operating.

(Server)

Figure 9:
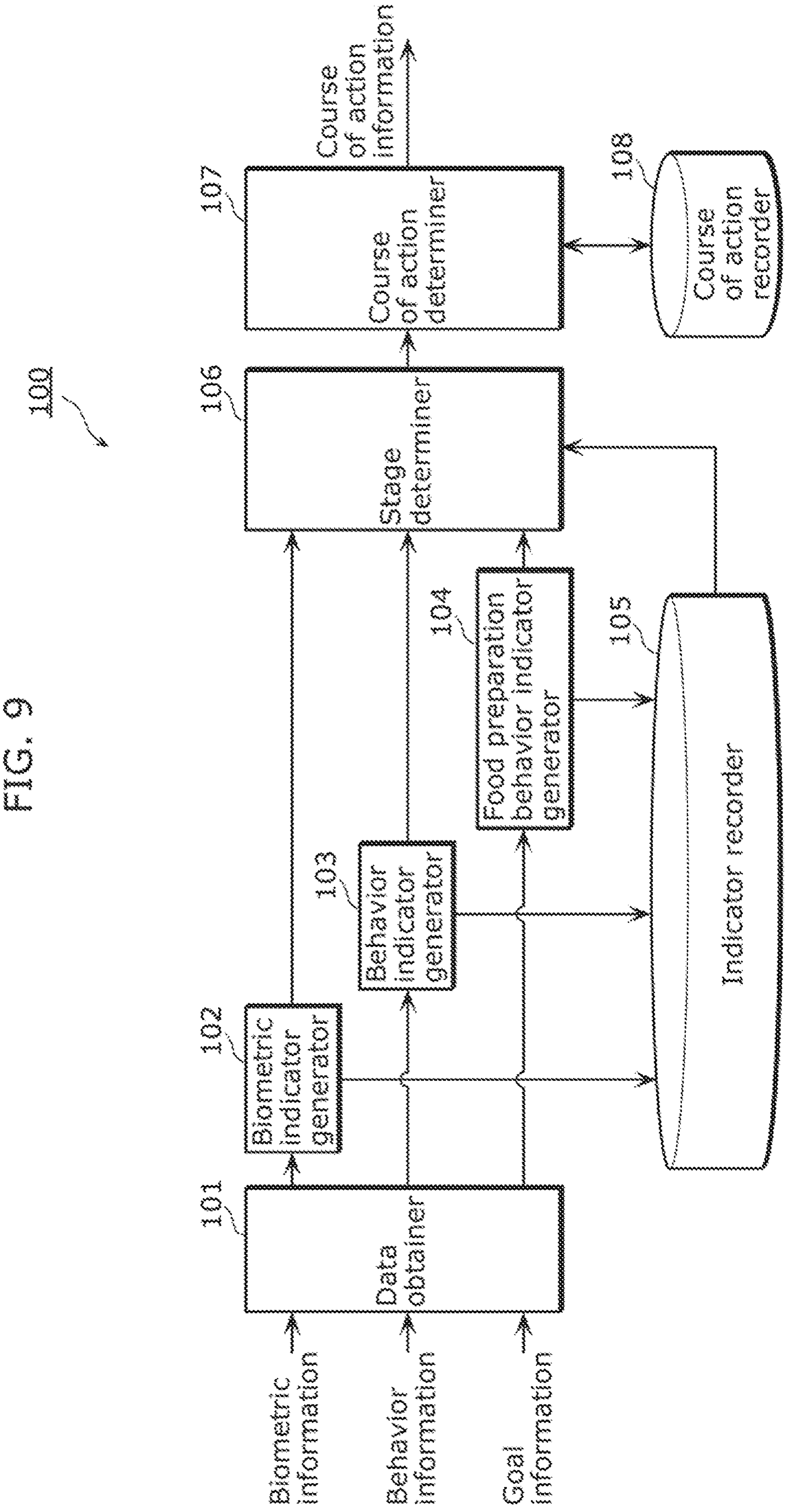
FIG. 9 is a block diagram illustrating an example of the configuration of a server according to an embodiment.

FIG. 9 is a block diagram illustrating an example of the configuration of server 100. As illustrated in FIG. 9, server 100 includes data obtainer 101, biometric indicator generator 102, behavior indicator generator 103, food preparation behavior indicator generator 104, indicator recorder 105, stage determiner 106, course of action determiner 107, and course of action recorder 108.

As mentioned above, support for preparing low-sodium meals requires support not only for the subject themselves, but also support for the food preparer. Therefore, based on the subject's health information and the stages of behavior change of the subject and the food preparer, dietary guidance system 10 provides support for food preparation and encouraging acceptance of low-sodium diets in accordance with the stages. Dietary guidance system 10 also provides meal proposals tailored to the condition/state of the subject and the food preparer. This allows the subject and the food preparer to become accustomed to a low-sodium diet in stages. This also enables the food preparer to learn to prepare food with less salt.

Data obtainer 101 obtains the subject's biometric information (for example, vital information such as blood pressure values), the subject's and the food preparer's behavior information (for example, whether salt intake is being actively reduced and low-sodium meal preparation skill), and goal information (for example, target values for each of a plurality of stages and a final goal). For example, this information is obtained from terminal device 300*a*, 300*b*, or 300*c*.

Biometric indicator generator 102 generates a biometric indicator for the subject based on the biometric information. Behavior indicator generator 103 generates a behavior indicator that represents the actual performance or accomplishment of an action that affects the subject's biometric indicator based on the behavior information. Food preparation behavior indicator generator 104 generates a food preparation behavior indicator that represents the actual performance or accomplishment of the food preparer's food preparation behavior with respect to low-sodium meals, based on the food preparer's behavior information. Indicator recorder 105 stores the biometric indicator generated by biometric indicator generator 102, the behavioral indicator generated by behavior indicator generator 103, and the food preparation behavior indicator generated by food preparation behavior indicator generator 104.

Stage determiner 106 determines the stage of behavior change of the subject and the food preparer based on the subject's and the food preparer's goal information, biometric indicators, behavior indicators, and food preparation behavior indicators.

Course of action recorder 108 stores courses of action for meals for each stage of behavior change. Here, a "course of action" specifically includes the food (dishes) to be served to the subject and the food preparer's food preparation tasks. For example, the food to be served to the subject is a single meal with the amount of salt, calories, sugar, and oil adjusted to match the biometric indicator, the behavior indicator, and the food preparation behavior indicator. A food preparation task includes whether or not food preparation is required, and the amount of food preparation steps required (degree of food preparation already done). For example, a course of action includes whether the subject and the food preparer are provided (for example, delivered) with a prepared edible (food), a semi-prepared edible (food), or an unprepared ingredient.

Course of action determiner 107 determines a course of action based on the stage of behavior change determined by stage determiner 106, referring to the information stored in course of action recorder 108. For example, course of action determiner 107 outputs course of action information indicating the determined course of action to at least one of terminal device 300*a* or terminal device 300*b*.

With this configuration, dietary guidance system 10 estimates the stage of behavior change based on the subject's vitals, awareness of salt-reduction behavior or health management, whether or not the behavior is implemented, and the food preparer's implementation of food preparation-related behavior (including food preparation skills), and makes it possible to provide the necessary dietary support in providing meals when adopting a low-sodium diet.

[Operations]

Figure 10:
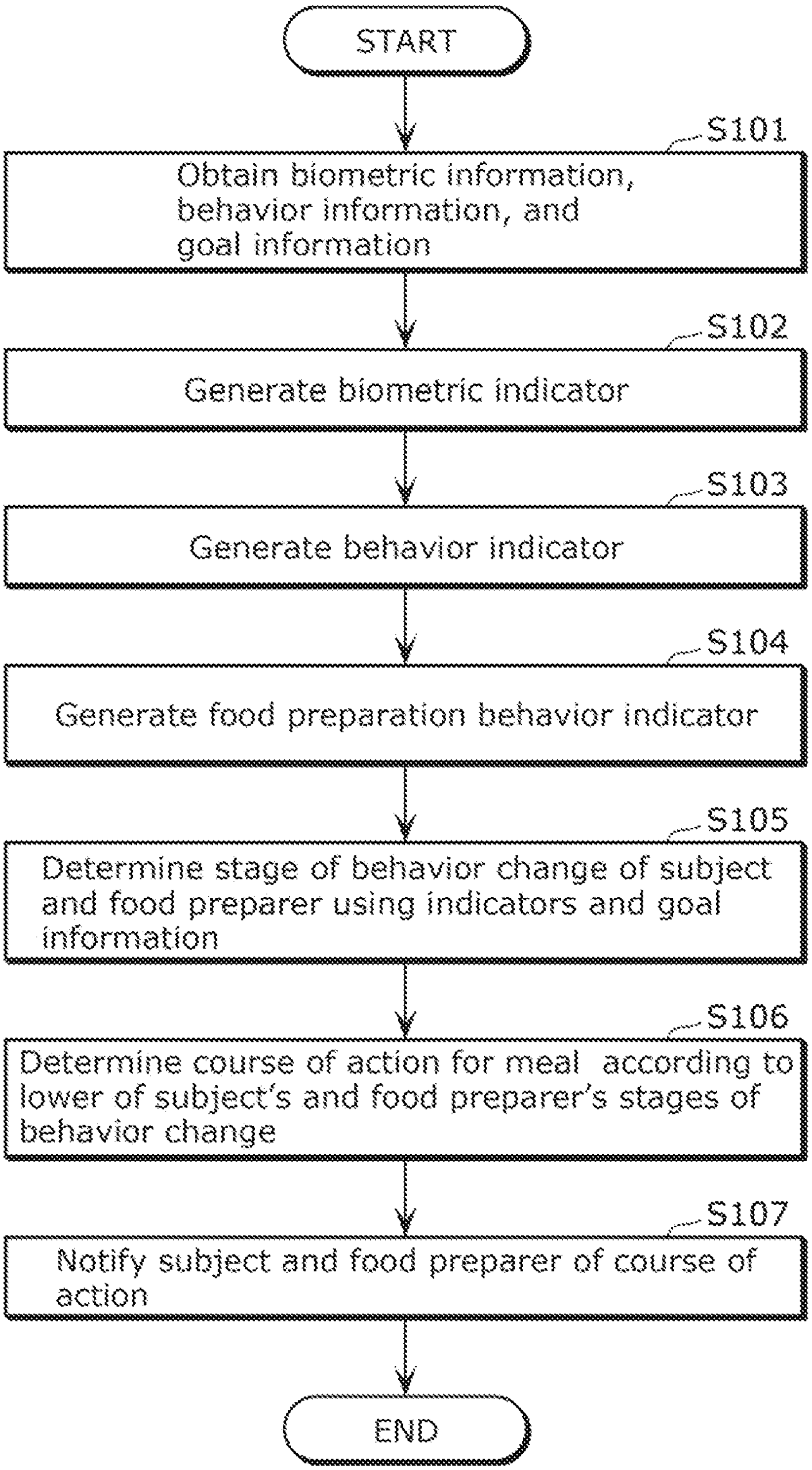
FIG. 10 is a flowchart illustrating operations performed by the server according to an embodiment.

FIG. 10 is a flowchart illustrating operations performed by server 100. First, data obtainer 101 obtains, for example, the subject's biometric information, the subject's and the food preparer's behavior information, and the goal information (S101). For example, this information is obtained from terminal device 300*a*, 300*b*, or 300*c*.

Biometric indicator generator 102 generates a biometric indicator for the subject based on the biometric information (S102). Behavior indicator generator 103 generates a behavior indicator for the subject based on the behavior information (S103). Food preparation behavior indicator generator 104 generates a food preparation behavior indicator based on the food preparer's behavior information (S104). The generation of the biometric indicator, the behavior indicator, and the food preparation behavior indicator need not be performed in the listed order, and may be performed in parallel.

Next, stage determiner 106 uses, for example, the subject's and the food preparer's goal information, biometric indicator, behavior indicator, and food preparation behavior indicator to determine the stage of behavior change of the subject and the stage of behavior change of the food preparer (S105).

Next, course of action determiner 107 determines a course of action for the meal according to the lower one of the subject's stage of behavior change or the food preparer's stage of behavior change determined by stage determiner 106 (S106).

Next, course of action determiner 107 outputs course of action information indicating the determined course of action to at least one of terminal device 300*a* or terminal device 300*b*, thereby notifying the subject and the food preparer of the determined course of action (S107).

EXAMPLES OF THE VARIOUS INFORMATION

FIG. 11 illustrates examples of the biometric information, behavior information, goal information, and other information obtained by data obtainer 101. The biometric information may include the subject's blood pressure and vital information. The biometric information may include medical checkup information, electronic medical records, or receipt information, such as height, weight, age, disease information, blood test data, hospital visit history, medical history, and medication information. The biometric information may also include an exercise routine, a sleep condition (sleep duration and quality), and a defecation status. The biometric information may include, but is not limited to, various biometric information of the subject that can be obtained in the future. For example, the vital information may include at least one of a pulse wave, a heart rate, an electrocardiogram, blood glucose, a step count, or an activity level.

The subject's behavior information includes information about the subject's reduction of salt intake. Behavior information may include food consumption information (time and content of breakfast, lunch, dinner, snacks, late-night meals, and alcohol consumption), eating out habits, frequency of eating out, occupation, whether a smoker or not, etc., which are included in the medical interview information. The food consumption information may include, for example, the frequency with which the subject takes pictures of meals they eat, pictures of meals, the frequency of eating out, the amount or frequency of snacking, and an evaluation of how the meals they eat taste. The food consumption information may include the dishes of a meal. Data obtainer 101 may also obtain the dishes of the meal as food consumption information by estimating the dishes from a photo of the meal. Data obtainer 101 may obtain the nutritional composition of a meal by estimating it from the dishes of the meal. Nutritional composition includes the amount of energy and salt content of the meal. The behavior information of the subject may include, but is not limited to, various information indicating behavior of the subject that can be obtained in the future.

The food preparer's behavior information includes information indicating the food preparer's shopping content, shopping frequency, whether or not a meal delivery service, etc., is used, whether or not health foods and supplements are used, time spent preparing food, equipment and appliances used in food preparation, seasoning preferences, and food preparation methods used during the week (made at home, taking out, eating out, etc.). The behavior information of the food preparer may include, but is not limited to, various information indicating behavior of the food preparer that can be obtained in the future.

The subject's behavior information and the food preparer's behavior information may include app information about the health management app on terminal device 300*a* or 300*b*. The app information includes the frequency with which the subject or the food preparer views the health management app and the amount of instructional content geared for the subject viewed in the health management app.

The subject's goal information indicates the subject's hobbies or the state the subject aspires to be in. The goal information may include, but is not limited to, information indicating various goals for the hypertensive subject that can be obtained in the future. The goal information of the food preparer includes information indicating the food preparer's hobbies, family structure, or the state the food preparer aspires to be in. The goal information of the food preparer may include, but is not limited to, information indicating various goals for the food preparer that can be obtained in the future.

Other information may be used. Other information is, for example, feedback information from the subject and the food preparer via applications running on terminal devices 300*a* and 300*b*. Such information is, for example, the subject's or food preparer's response to a question, specifically, a photographic response, or a response to a questionnaire. For example, the other information may include an evaluation of the meal (i.e., regarding seasoning (light, strong, etc.), quantity (too much, too little, etc.), appearance (balance, color, etc.)), and food preparation method (ease of preparation, accessibility of ingredients, etc.).

The biometric indicator may be an indicator obtained by statistical calculation or processing of a plurality of items of biometric information. Alternatively, if the period of time during which the subject's diet affects the biometric information is known, the biometric indicator may be calculated using the biometric information for that period. For example, if a factor known to affect blood pressure is salt, and blood pressure values are affected two days after high salt intake, the biometric indicator may be calculated using two days of biometric information. The method of calculating the biometric indicator may be set for each subject.

The behavior indicator may be an indicator obtained by statistical calculation or processing of a plurality of items of behavior information. Alternatively, the most recent behavior information may be used to calculate the behavior indicator. For example, the behavior indicator is generated based on the subject's behavior information for the most recent week, or the most recent five instances, etc.

The food preparation behavior indicator may be an indicator obtained by statistical calculation or processing of a plurality of items of behavior information. Alternatively, the most recent behavior information may be used to calculate the food preparation behavior indicator. For example, the food preparation behavior indicator is generated based on the food preparer's behavior information for the most recent week, or the most recent five instances, etc.

The statistical calculation described above may include averaging, extraction of the minimum value, the maximum value, the mode value, or the median value, etc. The processing described above may include normalization, quantization, merging of a plurality of data of different types (for example, exercise data and medication data), etc.

Although an example in which the indicators are calculated from various information is given here, the various information may be used as-is for stage determination, etc., without calculating the indicators.

(Stage Determination Process)

Figure 12:
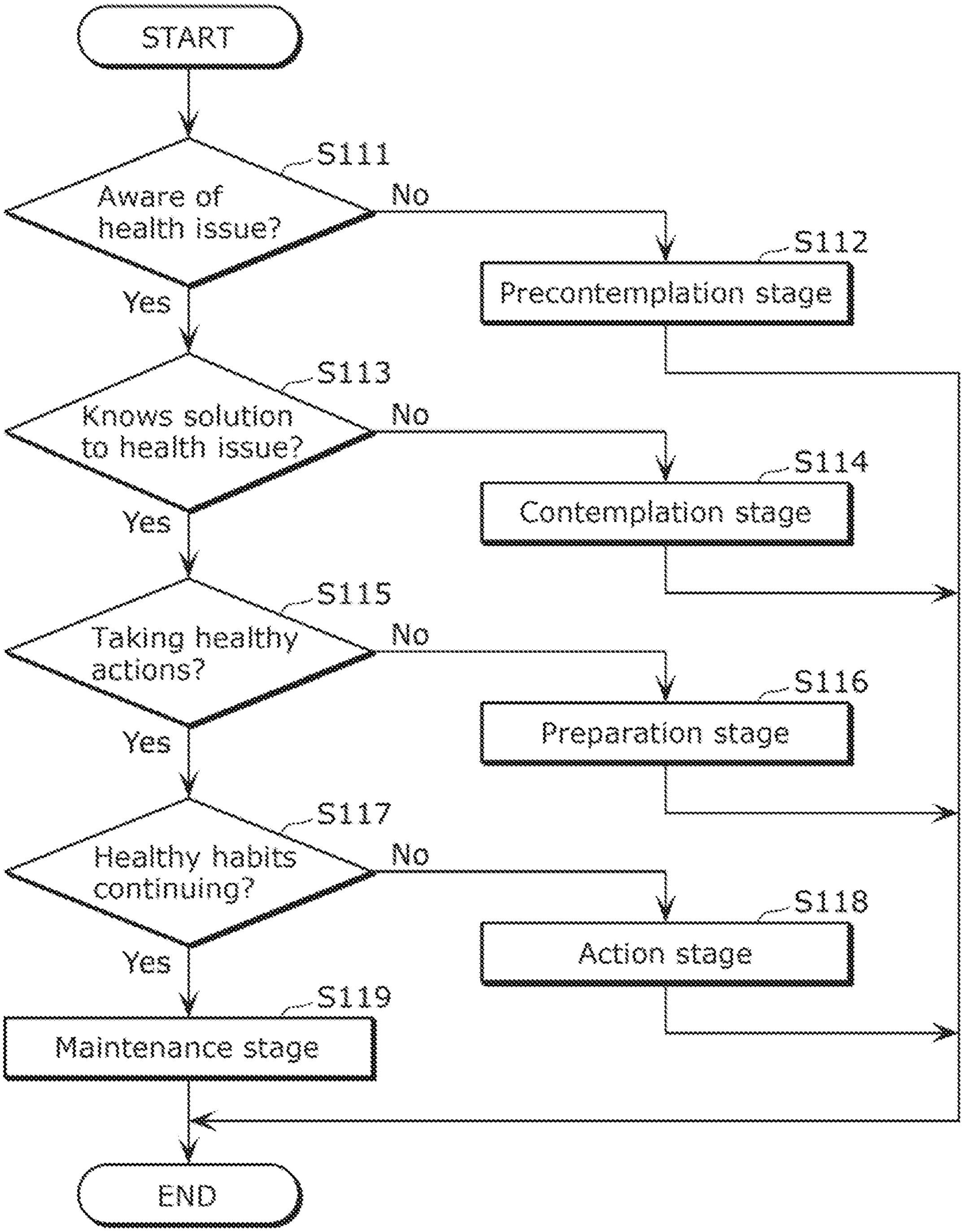
FIG. 12 is a flowchart illustrating one example of a stage determination process according to an embodiment.

FIG. 12 is a flowchart illustrating one example of a stage determination process performed by stage determiner 106. The process illustrated in FIG. 12 is performed on each of the subject and the food preparer to determine the stage of behavior change of each of the subject and the food preparer.

First, stage determiner 106 determines the stage of behavior change of each of the subject and the food preparer, using the current biometric indicator, behavior indicator, and food preparation behavior indicator, as well as previous records of the biometric indicator, the behavior indicator, and the food preparation behavior indicator, with respect to the goal information of the subject and the food preparer.

If stage determiner 106 determines that the subject is not aware of the health issue (No in S111), it determines that the subject's stage of behavior change is the precontemplation stage (S112). Similarly, if stage determiner 106 determines that the food preparer is not aware of the health issue (No in S111), it determines that the food preparer's stage of behavior change is the precontemplation stage (S112).

If stage determiner 106 determines that the subject is aware of the health issue (Yes in S111), but does not know the solution to the health issue (No in S113), it determines that the subject's stage of behavior change is the contemplation stage (S114). Similarly, if stage determiner 106 determines that the food preparer is aware of the health issue (Yes in S111), but does not know the solution to the health issue (No in S113), it determines that the food preparer's stage of behavior change is the contemplation stage (S114). For example, if the food preparer is interested in reducing salt because the subject has high blood pressure but does not know how to prepare the food, the food preparer's stage of behavior change is determined to be the contemplation stage because the food preparer does not know the solution to the health issue.

If determiner 106 determines that the subject knows the solution to the health issue (Yes in S113) but is not taking healthy actions (No in S115), it determines the subject's stage of behavior change to be the preparation stage (S116). Similarly, if determiner 106 determines that the food preparer knows the solution to the health issue (Yes in S113) but is not taking healthy actions (No in S115), it determines the food preparer's stage of behavior change to be the preparation stage (S116). For example, if the subject understands and grasps the need to eat a low-sodium diet, but is unable to take action (i.e., is not mindful when eating), the subject is not exhibiting health-improving behavior and the subject's stage of behavior change is determined to be the preparation stage.

If determiner 106 determines that the subject is exhibiting healthy behavior (Yes in S115) but is not continuing healthy habits (No in S117), it determines the stage of behavior change of the subject to be the action stage (S118). If determiner 106 determines that the food preparer is exhibiting healthy behavior (Yes in S115) but is not continuing healthy habits (No in S117), it determines the stage of behavior change of the food preparer to be the action stage (S118).

If stage determiner 106 determines that the subject is continuing their healthy habits (Yes in S117), it determines the stage of behavior change of the subject to be the maintenance stage (S119). Similarly, if stage determiner 106 determines that the food preparer is continuing their healthy habits (Yes in S117), it determines the stage of behavior change of the food preparer to be the maintenance stage (S119).

Stage determiner 106 may also obtain an evaluation of the subject's behavior by the food preparer or by the subject themselves, and further consider these evaluations when determining the subject's stage of behavior change. For example, stage determiner 106 may determine the subject's stage of behavior change to be the precontemplation stage based on an evaluation of unwillingness to eat recipes designed to improve health. For example, stage determiner 106 may determine the subject's stage of behavior change to be the contemplation stage based on an evaluation that the subject realizes that meals prepared with recipes designed to improve health are healthy (i.e., they show interest) but lack the knowledge of how or why they are healthy. For example, stage determiner 106 may determine the subject's stage of behavior change to be the preparation stage based on an evaluation that the subject is willing to eat meals prepared with recipes designed to improve health but is not acting on it (i.e., is not eating such meals). For example, stage determiner 106 may determine the subject's stage of behavior change to be the action stage based on an evaluation or a track record that the subject is eating meals prepared with recipes designed to improve health but is not satisfactorily feeling the health benefits. For example, stage determiner 106 may determine the subject's stage of behavior change to be the maintenance stage based on an evaluation or track record that the subject continues to eat meals prepared with recipes designed to improve health, snacks less than before, and has a daily energy and salt intake below a certain value.

Stage determiner 106 may also determine the stage of behavior change of the subject according to the status of registration of food consumption information and an evaluation thereof. For example, stage determiner 106 may determine the subject's stage of behavior change to be the precontemplation stage when no food consumption log photos are entered or no biometric information is recorded. For example, stage determiner 106 may determine the subject's stage of behavior change to be the contemplation stage based on an evaluation that the subject understands that keeping a food consumption log will provide meal content estimations or guidance, but does not understand why it is necessary for him or her to do so. For example, stage determiner 106 may determine the subject's stage of behavior change to be the preparation stage based on an evaluation that the subject is willing to keep a food consumption log but is not acting on it (i.e., has not kept a food consumption log). For example, stage determiner 106 may determine the subject's stage of behavior change to be the action stage based on an evaluation that the subject is keeping a food consumption log but is not satisfactorily feeling the effects. For example, stage determiner 106 may determine the subject's stage of behavior change to be the maintenance stage based on an evaluation that the subject is continuing to keep a food consumption log, has changed their meal content, or has reduced their estimated daily energy or salt intake to a certain value, or that the biometric information has changed.

Stage determiner 106 may also determine the stage of behavior change of the subject according to the status of registration of biometric information and an evaluation thereof. For example, stage determiner 106 may determine the subject's stage of behavior change to be the precontemplation stage based on an evaluation of unwillingness to register biometric information. For example, stage determiner 106 may determine the subject's stage of behavior change to be the contemplation stage based on an evaluation that the subject understands (was told by a doctor) that recording biometric information is necessary, but does not understand why it is necessary for him or her to do so. For example, stage determiner 106 may determine the subject's stage of behavior change to be the preparation stage based on an evaluation that the subject is willing to record biometric information but is not acting on it (i.e., has not recorded biometric information). For example, stage determiner 106 may determine the subject's stage of behavior change to be the action stage based on an evaluation that the subject has recorded biometric information but is not satisfactorily feeling the effects. For example, stage determiner 106 may determine the subject's stage of behavior change to be the maintenance stage based on an evaluation that the subject continues to record biometric information, or that the subject feels a change in biometric information, or that the subject understands the relationship (their body's unique relationship) between diet and biometric information.

Stage determiner 106 may obtain app information about the health management app on terminal device 300*b*. The app information includes the amount of time the food preparer views recipes designed to improve health (for example, low-sodium recipes) in the health management app on terminal device 300*b*, the frequency that the food preparer inputs information indicating that the food preparer cooked a meal using a recipe designed to improve health on that day, the frequency that the food preparer views the health management app, the amount of instructional content geared for the food preparer viewed by the food preparer in the health management app. Stage determiner 106 may also estimate the amount and rate of decrease in the use of seasonings, including salt, included in recipes cooked based on input history over a predetermined period of information in the health management app indicating that a meal using a recipe designed to improve health was prepared. Stage determiner 106 may estimate the cooking skill level of the food preparer based on the app information.

Stage determiner 106 may evaluate the stage of behavior change of the food preparer based on the app information obtained from terminal device 300*b*, and take the evaluation result as the stage of behavior change of the food preparer. Stage determiner 106 may determine the food preparer's stage of behavior change at predetermined intervals according to the app information from terminal device 300*b*. More specifically, stage determiner 106 may determine the food preparer's stage of behavior change such that a higher stage of behavior is adopted in correlation with an increase in the amount of time the food preparer views recipes designed to improve health in the health management app, an increase in the frequency that the food preparer inputs information indicating that the food preparer cooked a meal using a recipe designed to improve health on that day, an increase in at least one of frequency of opening the health management app or the amount of instructional content viewed in the health management app, a decrease in the amount and rate of decrease in the use of seasonings, including salt, included in recipes cooked, and an increase in cooking skill level.

Stage determiner 106 may also obtain an evaluation of the food preparer's behavior by the subject or by the food preparer themselves, and further consider these evaluations when determining the food preparer's stage of behavior change. For example, stage determiner 106 may determine the food preparer's stage of behavior change to be the precontemplation stage based on an evaluation of unwillingness to prepare recipes designed to improve health. For example, stage determiner 106 may determine the food preparer's stage of behavior change to be the contemplation stage based on an evaluation that the subject realizes that meals prepared with recipes designed to improve health are healthy (i.e., they show interest) but have a preconceived notion that they are not delicious or are too much trouble. For example, stage determiner 106 may determine the food preparer's stage of behavior change to be the preparation stage based on an evaluation that the food preparer is willing to cook meals prepared with recipes designed to improve health but is not acting on it (i.e., is not preparing such meals). For example, stage determiner 106 may determine the food preparer's stage of behavior change to be the action stage based on an evaluation or a track record that the food preparer is preparing meals with recipes designed to improve health but is not satisfactorily feeling the health benefits. For example, stage determiner 106 may determine the food preparer's stage of behavior change to be the maintenance stage based on an evaluation or a track record that the food preparer is continuing to prepare meals with recipes designed to improve health, does not mind reducing salt in their usual cooking, or thinks such meals taste good.

(Course of Action Example)

Figure 13:
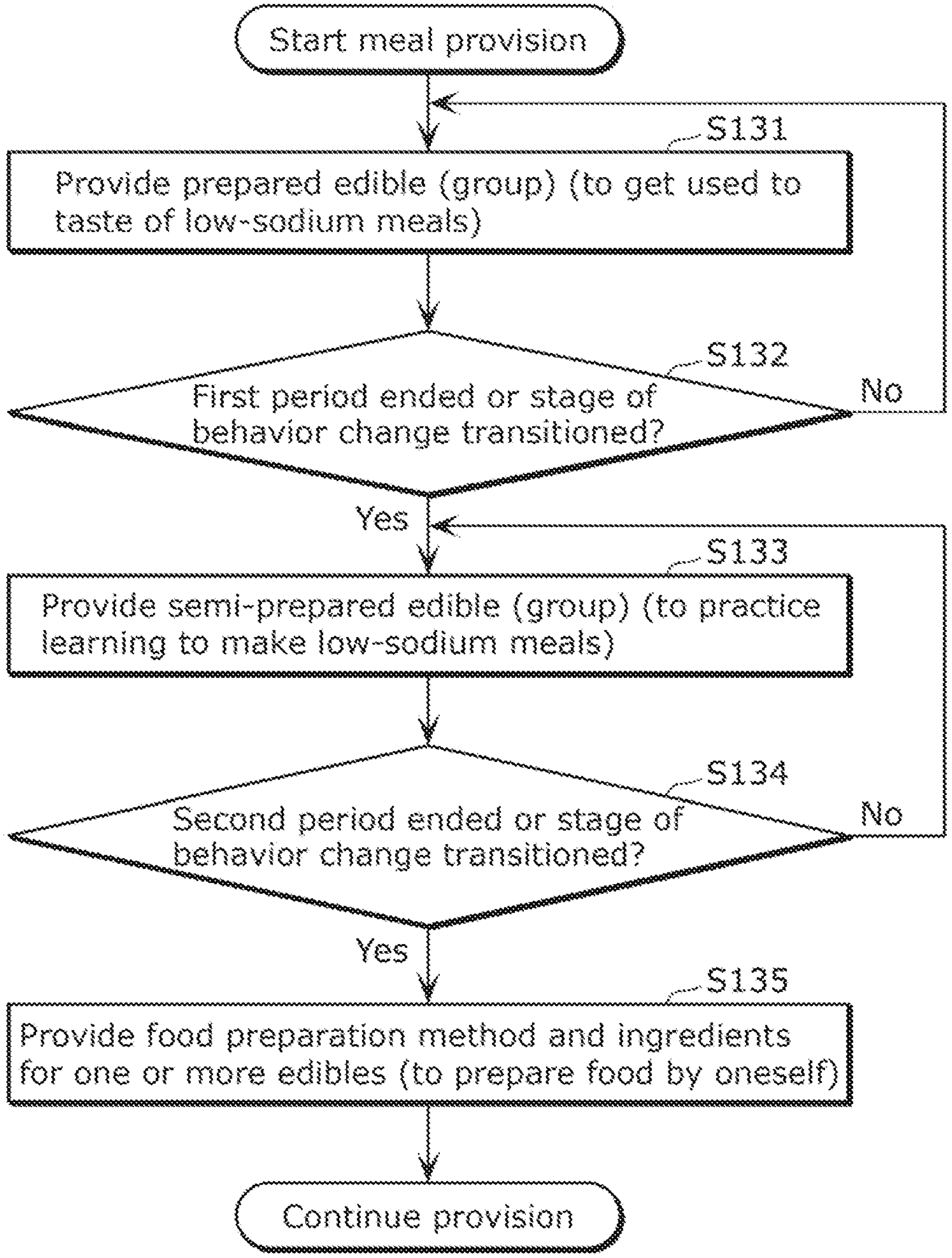
FIG. 13 is a flowchart illustrating a course of action determination process according to an embodiment.

FIG. 13 is a flowchart illustrating a course of action determination process performed by course of action determiner 107. FIG. 14 illustrates an example of a course of action.

Course of action determiner 107 determines a course of action according to the lower stage of behavior change between the subject's stage of behavior change and the food preparer's stage of behavior change determined by stage determiner 106. FIG. 14 illustrates an example where the first period corresponds to the contemplation stage, the second period corresponds to the preparation stage, and the third period corresponds to the action stage. For example, the first, second, and third periods are periods of defined length, for example, one week.

For example, if the lower stage of behavior change is determined by stage determiner 106 to be the contemplation stage, the provision of meals to the subject and food preparer is initiated. First, during the first period (the contemplation stage), a prepared edible (group) is provided to the subject and the food preparer to help them get used to the taste of low-sodium meals (S131). A prepared edible is prepared food. Accordingly, the food preparer is not required to prepare food during this period.

For example, the determined prepared food is displayed on subject's or the food preparer's terminal device 300*a* or 300*b*, and information about the website of a delivery service where the food can be ordered (for example, a link to a webpage where the food can be ordered) is displayed. This allows the food preparer to access the website and order the food. Here, a plurality of types of low-sodium food may be displayed, and the subject or food preparer may select the food to order from among the displayed food.

The food provided by the system may be for every meal for the subject, for a portion of the day (for example, only dinner), or for a number of days. All of the food in a single meal may be provided, and, alternatively, only some of the food in a single meal may be provided. Furthermore, only those foods to be eaten by the subject may be provided, and, alternatively food for a plurality of people including the subject and the food preparer may be provided.

The presentation and ordering in this course of action may be done for each meal, and, alternatively, a plurality of meals (for example, a weeks' worth of meals) may be ordered together.

Note that prepared edibles are not limited to food that does not require any work by the food preparer or subject, and may also include food in which some work is carried out. For example, the work may include warming the food by microwave or hot water, pouring enclosed sauce or condiments on the food, cutting the food to make it easier to eat, etc.

Dietary guidance system 10 may include a home delivery service, and the food may be provided via the home delivery service.

If the set first period has not ended and the stage of behavior change has not changed (No in S132), the prepared edible (group) is still provided at the next meal (S131).

The transition of the stage of behavior change from the contemplation stage to the preparation stage can be determined based on changes in behavior information or biometric information. For example, a transition between stages may be determined to occur when there is a change in behavior information such as a change in usual food choices (for example, less use of condiments at lunch, less frequent selection of high-sodium prepared edibles, etc.). Alternatively, a transition between stages may be determined when there is a change in biometric information, such as a decrease in a blood pressure value or weight loss.

However, if the set first period has ended, or if the stage of behavior change has transitioned from the contemplation stage to the preparation stage (Yes in S132), a semi-prepared edible (group) is provided to help the food preparer learn to prepare a low-sodium meal at the next meal (S133).

A semi-prepared edible is an edible that has been prepared up to a portion of the steps. Stated differently, for the same food, a semi-prepared edible is an edible that has more food preparation steps (food preparation tasks) than a prepared edible. For example, a semi-prepared edible may include pre-measured seasoning. Alternatively, the semi-prepared edible may contain seasoned ingredients that require preparation. Alternatively, the semi-prepared edible may include one or more prepared edible dishes, and ingredients for the remaining dishes.

The method of providing the semi-prepared edible is the same as the method of providing the prepared edible, but if the method of providing the semi-prepared edible includes ingredients or seasonings, such ingredients or seasonings may be home delivered, and, alternatively, instead of being home delivered, the required ingredients or seasonings and their amounts may be indicated. In the latter case, for example, the food preparer may use ingredients or seasonings available at home or may purchase ingredients or seasonings at any store.

If the set second period has not ended and the stage of behavior change has not changed (No in S134), the semi-prepared edible (group) is still provided at the next meal (S133).

The transition of the stage of behavior change from the preparation stage to the action stage can be determined based on changes in behavior information or biometric information. For example, a transition between stages may be determined when there is a change in the food preparer's behavior information, such as a decrease in the amount of seasoning used or employing a food preparation method that uses seasonings other than salty (for example, spicy or umami) in the food preparer's usual food preparation. Alternatively, a transition between stages may be determined when there is a change in the subject's biometric information, such as a decrease in a blood pressure value or weight loss, throughout the first and second periods.

However, if the set second period has ended, or if the stage of behavior change has transitioned from the preparation stage to the action stage (Yes in S134), in order for the food preparer to prepare the low-sodium meals themselves at the next meal, cooking methods and ingredients for the edible are provided as a meal provision (S135).

The edible provided in the third period is not limited to certain food preparation methods or ingredients. For example, with respect to the same food, the edible provided in the third period may be one with more food preparation tasks than the edible provided in the second period.

The method of providing the food preparation method and ingredients in the third period may be the same as the method of providing the food preparation method and ingredients for the prepared edible. Alternatively, instead of being home delivered, the required ingredients or seasonings and their amounts may be indicated. In such cases, for example, the food preparer may use ingredients or seasonings available at home or may purchase ingredients or seasonings at any store.

Thereafter, the provision of food preparation methods and ingredients (S135) continues. More specifically, the provision of food preparation methods and ingredients (S135) continues even after the end of the predetermined third period or after the stage of behavior change transitions from the action stage to the maintenance stage.

For example, the transition from the action stage to the maintenance stage can be determined based on changes in behavior information or biometric information. For example, the stage may be determined to have transitioned if there is a change in the food preparer's behavior information, such as the adoption of low-sodium food preparation in the food preparer's usual food preparation. Alternatively, a transition between stages may be determined when there is a change in the subject's biometric information, such as a decrease in a blood pressure value or weight loss, throughout the first, second, and third periods.

Here, the food (group) served in the first, second and third periods include the same food. Stated differently, in each period, prepared edibles, semi-prepared edibles, food preparation methods, and ingredients of the same food are provided. All periods do not necessarily have to include the same food; two or more periods may include the same food.

The length of the first and second periods may be set by the subject or the food preparer, by the instructor (physician or nutritionist, etc.), or by a family member living with the subject.

As described above, dietary guidance system 10 according to the present embodiment determines a course of action for the subject's food based on the lower one of the subject's stage of behavior change or the food preparer's stage of behavior change. With this, by using a course of action suited to the individual at the lower stage of behavior change, it is possible to inhibit a decline in motivation of the individual at the lower stage of behavior change and effectively raise their stage of behavior change. This allows dietary guidance system 10 to effectively provide dietary guidance.

In the first, second, and third periods, a prepared edible, a semi-prepared edible or ingredients, and unprepared ingredients are provided, respectively. With this, in low stages of behavior change in particular, the food preparer's effort can be reduced, thus maintaining or increasing the food preparer's motivation to continue dietary guidance. In particular, by the food preparer's effort increasing gradually, the food preparer's motivation to continue dietary guidance can be maintained or increased.

In the first period, the subject and the food preparer may, for example, test how the low-sodium meals taste. This allows, for example, the food preparer to prepare food in the second or third period that suits the subject's palate out of the food served in the first period. This inhibits the lowering of the food preparer's motivation due to food that the food preparer has spent a lot of time and effort to prepare not being to the subject's liking. In addition, since the subject and the food preparer can become accustomed to the taste of low-sodium meals during the first period, food not being suitable to the subject's palate during the second or third period can be inhibited. Furthermore, once prepared food is provided, even if the food preparation in the second or third period is not done well, the subject can recognize that there is a problem with the food preparation rather than with the low-sodium meal itself, thus inhibiting the low-sodium meal itself from being negatively evaluated. In this way, dietary guidance system 10 can effectively provide dietary guidance.

[Variation 1]

Figure 15:
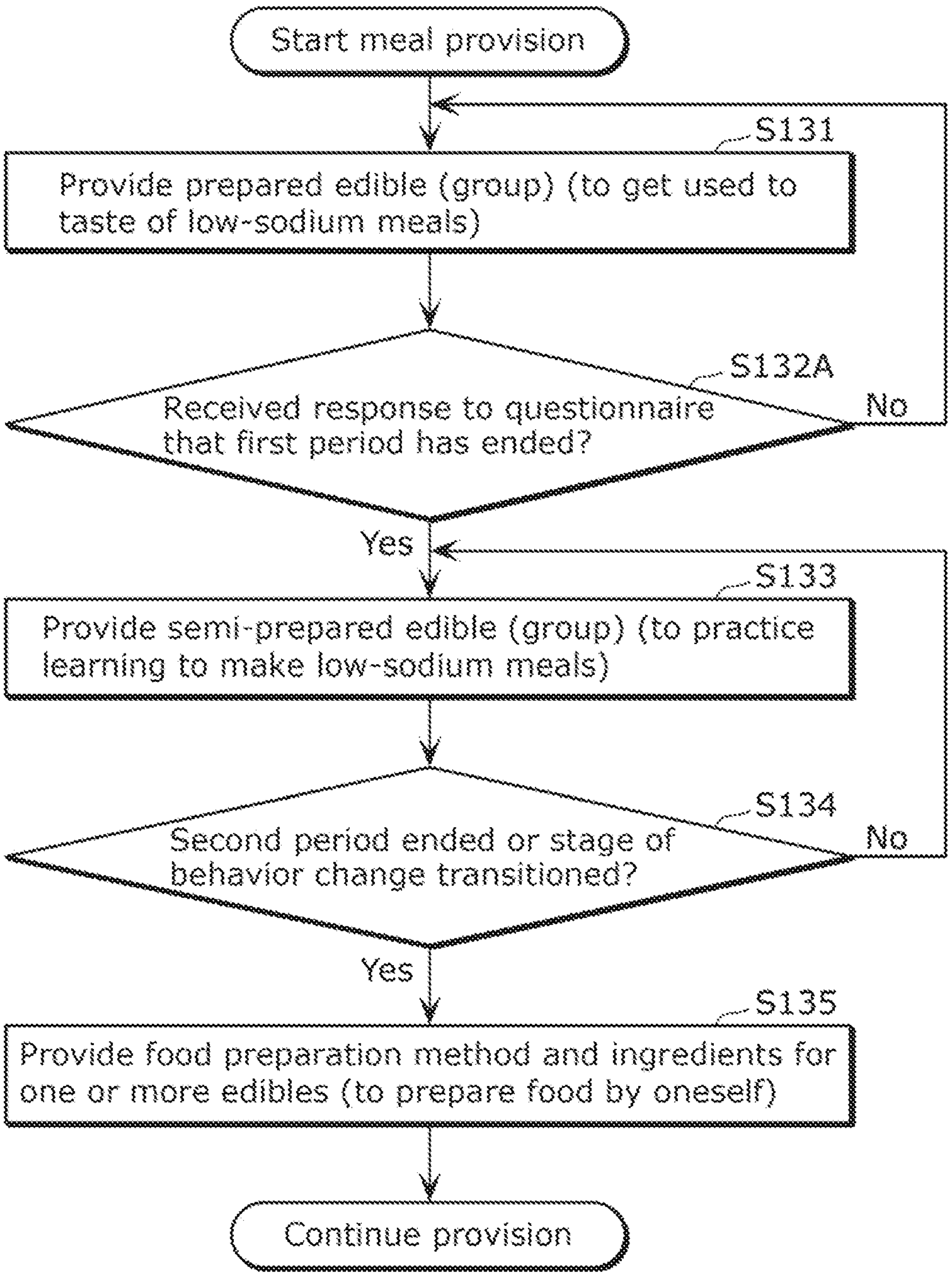
FIG. 15 is a flowchart illustrating a variation of a course of action determination process according to an embodiment.

The determination in step S132 illustrated in FIG. 13 may be based on responses to a questionnaire by the subject and the food preparer. FIG. 15 is a flowchart illustrating a course of action determination process performed by course of action determiner 107 in such a case. The process illustrated in FIG. 15 differs from the process illustrated in FIG. 13 in that step S132 is replaced by step S132A.

As illustrated in FIG. 15, server 100 may determine that the first period has ended (i.e., may determine to proceed to the next stage) if it receives a response (Yes in S132A) to the questionnaire by the subject and the food preparer that the first period has ended (i.e., a response to proceed to the next stage). The survey may be conducted every time a period set as the first period (for example, one week) elapses.

In the questionnaire, whether to end the first period may be answered directly, and, alternatively, whether to end the first period may be determined based on the responses to the questionnaire. For example, the subject and the food preparer may move to the next stage when they have confirmed that they no longer have a negative perception of the taste of low-sodium meals, or that they feel the seasoning of conventional or restaurant meals is too salty.

In FIG. 15, only step S132 is replaced, but responses to the questionnaire by the subject and the food preparer may be used in step S134 as well. In such cases, for example, the food preparer may move to the next stage when it can be confirmed that the food preparer has learned about seasoning amount or methods of normally used seasonings.

Similarly, whether to end the third period may be based on responses to a questionnaire by the subject and the food preparer. The questionnaire may be administered to one of the subject or the food preparer.

In addition, in determining each period, transitioning between stages may be determined by taking into account both the determination based on the behavior information or biometric information described above and the questionnaire responses.

[Variation 2]

FIG. 16 illustrates a variation of courses of action provided in each period. As illustrated in FIG. 16, for example, either the first period (provision of prepared edibles) or the second period (provision of semi-prepared edibles) may be used. For example, one of these periods is included in the contemplation stage.

The third period may correspond to the preparation stage and the action stage. In this case, as illustrated in FIG. 16, before the food preparation method is presented, the subject and the food preparer may be presented with a food preparation or eating method that focuses on serving, for example, "reduce the amount of soup to half", "reduce the frequency of fried foods", or "increase dishes including fish with a bluish back" in the first half of the preparation period.

In the later portion of the preparation stage, a salt-free or low-salt alternative may be presented to the subject and the food preparer. This allows the subject to reduce salt intake even if a low-sodium dish is not used, achieving a reduction in salt intake. It also allows the subject to avoid hunger due to insufficient amounts of food.

[Variation 3]

FIG. 17 illustrates a variation of courses of action provided in each period. As illustrated in FIG. 17, for example, either the first period (provision of prepared edibles) or the second period (provision of semi-prepared edibles) may be used. For example, one of these periods is included in the contemplation stage. In the example illustrated in FIG. 17, the third period corresponds to the preparation stage.

Whether to use the first period (provision of prepared edibles) or the second period (provision of semi-prepared edibles), or whether to use both may be set according to the subject's or food preparer's wishes.

[Variation 4]

Figure 18:
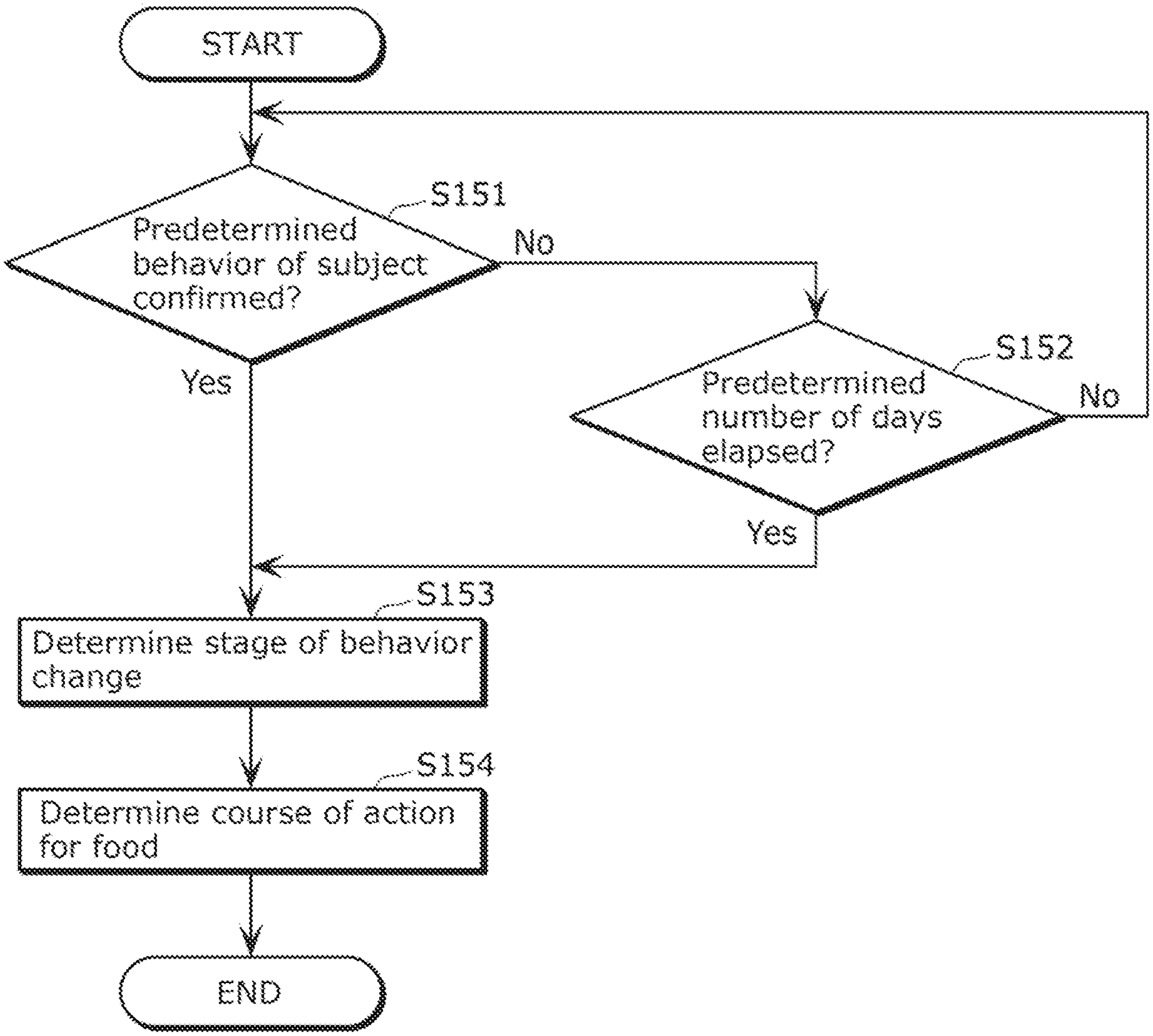
FIG. 18 is a flowchart illustrating an example of the timing for determining the stage of behavior change and determining a course of action according to an embodiment.

FIG. 18 is a flowchart illustrating an example of the timing for determining the stage of behavior change and determining the course of action described above.

As illustrated in FIG. 18, server 100 may determine the stage of behavior change (S153) and determine the course of action for food (S154) when a predetermined behavior of the subject is confirmed (Yes in S151) or when a predetermined number of days (for example, one week) have elapsed (Yes in S152).

Here, the predetermined behavior detected in step S151 is, for example, a behavior that affects the subject's blood pressure, such as high salt intake. The prescribed behavior may be a behavior specified in guidance information, such as smoking or heavy drinking. The detection of these behaviors is based on the subject's behavior information, for example. For example, a given behavior is detected when the food consumption information indicates that the above predetermined behavior has been exhibited.

With this, dietary guidance system 10 can promptly provide feedback to the subject and the food preparer, for example, when it detects a predetermined behavior that affects the subject's physical condition, etc. This makes it possible to inhibit the subject from exhibiting a predetermined behavior, and quickly determine an appropriate course of action.

(Other Variations)

In the above description, server 100 has a function to determine the stages of behavior change of the subject and the food preparer, but it may obtain the stages of behavior change of the subject and the food preparer determined by other devices without such function.

The configuration illustrated in FIG. 7, etc., is one example, and some or all of the functions included in server 100 described above may be included in other devices (for example, terminal device 300*a* or 300*b*).

In the above description, displaying information is given as one example of a method of notifying the subject or food preparer with information, but the subject or food preparer may be notified with this information via voice or other some other method.

In the configuration illustrated in FIG. 7, etc., an example in which the subject and the food preparer use different terminal devices 300*a* and 300*b*, respectively, is given, but the subject and the food preparer may use the same terminal device, and, alternatively, only one of the subject or the food preparer may operate a terminal device. Stated differently, dietary guidance system 10 may include a terminal device used by at least one of the subject or the food preparer.

SUMMARY

As described above, dietary guidance system 10 according to the present embodiment includes an obtainer (for example, stage determiner 106) that obtains the first stage of behavior change defined as a stage of behavior change of the subject of dietary guidance and the second stage of behavior change defined as a stage of behavior change of the food preparer who prepares the subject's meals, and a determiner (for example, course of action determiner 107) that determines a course of action for the subject's meals based on the third stage of behavior change, which is the lower one of the first stage of behavior change or the second stage of behavior change.

With this, a course of action related to the food for the subject is determined based on a third stage of behavior change defined as a lower one of the first stage of behavior change or the second stage of behavior change. Accordingly, by using a course of action suited to the individual at the lower stage of behavior change, it is possible to inhibit a decline in motivation of the individual at the lower stage of behavior change and effectively raise their stage of behavior change. This allows dietary guidance system 10 to effectively provide dietary guidance.

For example, as illustrated in FIG. 14, FIG. 16 and FIG. 17, when the third stage of behavior change is a first stage, the determiner (for example, course of action determiner 107) determines, as the course of action, a first course of action related to preparing the subject's food, and when the third stage of behavior change is a second stage higher than the first stage, determines, as the course of action, a second course of action related to preparing the subject's food. The first course of action requires less preparation by the food preparer than the second course of action. With this, dietary guidance system 10 can provide a course of action suited to the stage of behavior change. In low stages of behavior change in particular, the food preparer's effort can be reduced, thus maintaining or increasing the food preparer's motivation to continue dietary guidance.

For example, as illustrated in FIG. 14, when the third stage of behavior change is a third stage higher than the second stage, the determiner (for example, course of action determiner 107) determines, as the course of action, a third course of action related to preparing the subject's food, and the third course of action requires more preparation by the food preparer than the second course of action.

With this, dietary guidance system 10 can provide a course of action suited to the stage of behavior change. In particular, by the food preparer's effort increasing gradually, the food preparer's motivation to continue dietary guidance can be maintained or increased.

For example, as illustrated in FIG. 14, the first course of action is providing the subject and the food preparer with prepared food, the second course of action is providing the food preparer with a partially prepared ingredient and having the food preparer carry out partial food preparation, and the third course of action is providing the food preparer with an unprepared ingredient and having the food preparer carry out food preparation. With this, the dietary guidance system can provide a course of action suited to the stage of behavior change.

For example, the partially prepared ingredient includes pre-measured seasoning. With this, the dietary guidance system can effectively reduce the food preparer's effort.

For example, the same food is provided to the subject in the first course of action and the second course of action. With this, the dietary guidance system allows the subject to try out and get used to foods at a lower stage which requires less food preparation. It is therefore possible to inhibit the occurrence of food that is not to the subject's taste, etc., after much effort has been taken to prepare it, thereby maintaining or improving the food preparer's and the subject's motivation to continue their dietary guidance.

For example, the obtainer (for example, stage determiner 106) obtains the first stage of behavior change and the second stage of behavior change by determining the first stage of behavior change based on at least one of behavior information, biometric information, or goal information of the subject and determining the second stage of behavior change based on at least one of behavior information or goal information of the food preparer. For example, as illustrated in FIG. 18, the obtainer (for example, stage determiner 106) updates the first stage of behavior change and second stage of behavior change upon each elapse of a predetermined number of days, and the determiner (for example, course of action determiner 107) updates the course of action upon each elapse of the predetermined number of days.

With this, dietary guidance system 10 can regularly update the stage of behavior change and the course of action.

For example, as illustrated in FIG. 18, if it is confirmed that a predetermined action has been taken based on the behavior information of the subject, (i) the obtainer (for example, stage determiner 106) updates the first stage of behavior change and second stage of behavior change regardless of the elapse of a predetermined number of days, and (ii) the determiner (for example, course of action determiner 107) updates the course of action regardless of the elapse of the predetermined number of days.

With this, dietary guidance system 10 can promptly provide feedback to the subject and the food preparer, for example, when it detects a predetermined behavior that affects the subject's physical condition, etc. This makes it possible to inhibit the subject from exhibiting a predetermined behavior, and quickly determine an appropriate course of action. For example, the predetermined behavior includes high salt intake.

The terminal device (for example, terminal device 300*a* or 300*b*) according to the present embodiment includes an obtainer (for example, communicator 312) that obtains information indicating a course of action that is related to food for a subject of dietary of guidance and determined based on a third stage of behavior change defined as a lower one of a first stage of behavior change of defined as a stage of behavior change the subject or a second stage of behavior change defined as a stage of behavior change of a food preparer who prepares the subject's food, and a presenter (for example, display 318) that presents the course of action to the subject or the food preparer.

With this, a course of action related to the food for the subject is determined based on a third stage of behavior change defined as a lower one of the first stage of behavior change or the second stage of behavior change. Accordingly, by using a course of action suited to the individual at the lower stage of behavior change, it is possible to inhibit a decline in motivation of the individual at the lower stage of behavior change and effectively raise their stage of behavior change. This allows the dietary guidance system that uses the terminal device to effectively provide dietary guidance.

[Other Comments]

Each of the elements in each of the above-described embodiments may be implemented as dedicated hardware, or may be realized by executing a software program suitable for the element. Each of the elements may be realized by way of a program executing unit, such as a CPU or a processor, reading and executing the software program recorded on a recording medium such as a hard disk or a semiconductor memory.

The present disclosure may be realized as the above program (software program). The program may be executed by being downloaded from a server or the like, or by reading the program recorded on a predetermined recording medium (for example, an optical disk such as a CD-ROM, a magnetic disk, semiconductor memory, etc.).

The computer executing the program may be a single computer or a plurality of computers. Stated differently, the process may be centralized or distributed.

The present disclosure may be realized as the above method. The present disclosure may also be realized as a computer program that implements these methods by computer, or as a digital signal of the above computer program.

As described above, embodiments have been described as examples of techniques according to the present disclosure. The accompanying drawings and detailed description are provided for this purpose.

Therefore, elements described in the accompanying drawings and the detailed description include, in addition to elements essential to overcoming the technical problem, elements that are not essential to overcoming the technical problem but are included in order to exemplify the techniques described above. As such, description of these non-essential elements in the accompanying drawings and the detailed description should not be taken to mean that these non-essential elements are essential.

The above embodiments are for providing examples of the techniques according to the present disclosure, and thus various modifications, substitutions, additions, and omissions are possible within the scope of the claims and equivalents thereof.

INDUSTRIAL APPLICABILITY

The present disclosure is applicable to dietary guidance systems, etc.

The invention claimed is:

1. A dietary guidance system comprising:
- a first blood pressure measurement device worn by a subject of dietary guidance;
- a second blood pressure measurement device worn by a food preparer who prepares food for the subject;
- a display;
- one or more memories; and
- at least one processor coupled to at least one of the one or more memories and configured to:
- determine (1) a subject's stage of behavior change defined as a stage of behavior change of the subject, as one of a plurality of predefined stages arranged in a predetermined order, based on a subject's blood pressure obtained by the first blood pressure measurement device and (2) a preparer's stage of behavior change defined as a stage of behavior change of the food preparer, as one of the plurality of predefined stages arranged in the predetermined order, and determined based on a preparer's blood pressure obtained by the second blood pressure measurement device;
- determine a course of action related to the food for the subject based on a lower stage of behavior change, wherein the lower stage of behavior change is defined as at least one of the subject's stage of behavior change or the preparer's stage of behavior change that is ranked lower in the predetermined order; and
- cause the display to display the course of action to the subject or the food preparer.

2. The dietary guidance system according to claim 1, wherein the at least one processor is further configured to:
- when the lower stage of behavior change is a first lowest stage, determine, as the course of action, a first course of action related to preparing the food for the subject,
- when the lower stage of behavior change is a second lowest stage higher than the first lowest stage, determine, as the course of action, a second course of action related to preparing the food for the subject, wherein the first course of action requires less preparation by the food preparer than the second course of action.

3. The dietary guidance system according to claim 2, wherein the at least one processor is further configured to:
- when the lower stage of behavior change is a third lowest stage, determine, as the course of action, a third course of action related to preparing the food for the subject, wherein the third course of action requires more preparation by the food preparer than the second course of action.

4. The dietary guidance system according to claim 3, wherein
- the first course of action is providing the subject and the food preparer with prepared food,
- the second course of action is providing the food preparer with a partially prepared ingredient and having the food preparer carry out partial food preparation, and the third course of action is providing the food preparer with an unprepared ingredient and having the food preparer carry out food preparation.

5. The dietary guidance system according to claim 4, wherein the partially prepared ingredient includes pre-measured seasoning.

6. The dietary guidance system according to claim 2, wherein a same food is provided to the subject in the first course of action and the second course of action.

7. The dietary guidance system according to claim 1, wherein the at least one processor is further configured to:

update the subject's stage of behavior change and the preparer's stage of behavior change upon each elapse of a predetermined number of days, and update the course of action upon each elapse of the predetermined number of days.

8. The dietary guidance system according to claim 7, wherein the at least one processor is further configured to:

on condition of confirmation of the subject exhibiting a predetermined behavior based on behavior information, (i) update the subject's stage of behavior change and the preparer's stage of behavior change regardless of the elapse of the predetermined number of days and (ii) update the course of action regardless of the elapse of the predetermined number of days.

9. The dietary guidance system according to claim 8, wherein the predetermined behavior includes high salt intake.

10. A portable terminal connected to a server over a network, the server including:

one or more first memories; and at least one first processor coupled to at least one of the one or more first memories and configured to:

obtain information indicating a course of action that is related to food for a subject of dietary guidance and determined based on a lower stage of behavior change, wherein the lower stage of behavior change is defined as at least one of (1) a subject's stage of behavior change defined as a stage of behavior change of the subject, as one of a plurality of predefined stages arranged in a predetermined order, and determined based on a subject's blood pressure obtained by a first blood pressure measurement device or (2) a preparer's stage of behavior change defined as a stage of behavior change of a food preparer who prepares food for the subject, as one of the plurality of predefined stages arranged in the predetermined order, and determined based on a preparer's blood pressure obtained by a second blood pressure measurement device that is ranked lower in the predetermined order; and generate a signal to display the course of action to the subject or the food preparer, the portable terminal comprising:

a display;

one or more second memories; and at least one first processor coupled to at least one of the one or more second memories and configured to:

receive the signal; and cause the second display to display presentation information based on the signal.

11. A control method of a dietary guidance system including one or more processors, the control method comprising, executed by the one or more processors:

obtaining (1) a subject's stage of behavior change defined as a stage of behavior change of the subject, as one of a plurality of predefined stages arranged in a predetermined order, and determined based on a subject's blood pressure obtained by a first blood pressure measurement device and (2) a preparer's stage of behavior change defined as a stage of behavior change of a food preparer who prepares food for the subject, as one of the plurality of predefined stages arranged in the predetermined order, and determined based on a preparer's blood pressure obtained by a second blood pressure measurement device;

determining a course of action related to the food for the subject based on a lower stage of behavior change, wherein the lower stage of behavior change is defined as at least one of the subject's stage of behavior change or the preparer's stage of behavior change that is ranked lower in the predetermined order;

generating a signal to display the course of action to the subject or the food preparer; and output the signal.

12. A control method of a dietary guidance system including a display, one or more processors, the control method comprising, executed by the one or more processors:

obtaining a course of action that is related to food for a subject of dietary guidance and determined based on a lower stage of behavior change, wherein the lower stage of behavior change is defined as a one of (1) a subject's stage of behavior change defined as a stage of behavior change of the subject, as one of a plurality of predefined stages arranged in a predetermined order, and determined based on a subject's blood pressure obtained by a first blood pressure measurement device or (2) a preparer's stage of behavior change defined as a stage of behavior change of a food preparer who prepares food for the subject, as one of the plurality of predefined stages arranged in the predetermined order, and determined based on a preparer's blood pressure obtained by a second blood pressure measurement device that is ranked lower in the predetermined order; and presenting, on the display, information about the course of action to the subject or the food preparer.

13. A non-transitory computer-readable recording medium having recorded thereon a program for causing operations comprising:

obtaining (1) a subject's stage of behavior change defined as a stage of behavior change of the subject, as one of a plurality of predefined stages arranged in a predetermined order, and determined based on a subject's blood pressure obtained by a first blood pressure measurement device and (2) a preparer's stage of behavior change defined as a stage of behavior change of a food preparer who prepares food for the subject, as one of the plurality of predefined stages arranged in the predetermined order, and determined based on a preparer's blood pressure obtained by a second blood pressure measurement device;

determining a course of action related to the food for the subject based on a lower stage of behavior change, wherein the lower stage of behavior change is defined as at least one of the subject's stage of behavior change or the preparer's stage of behavior change that is ranked lower in the predetermined order;

generating a signal to display the course of action to the subject or the food preparer; and output the signal.

14. A non-transitory computer-readable recording medium having recorded thereon a program for causing operations comprising:

obtaining a course of action that is related to food for a subject of dietary guidance and determined based on a lower stage of behavior change, wherein the lower stage of behavior change is defined as at least one of (1) a subject's stage of behavior change defined as a stage of behavior change of the subject, as one of a plurality of predefined stages arranged in a predetermined order, and determined based on a subject's blood pressure obtained by a first blood pressure measurement device or (2) a preparer's stage of behavior change defined as a stage of behavior change of a food preparer who prepares food for the subject, as one of the plurality of predefined stages arranged in the predetermined order, and determined based on a preparer's blood pressure obtained by a second blood pressure measurement device that is ranked lower in the predetermined order; and presenting, on the display, information about the course of action to the subject or the food preparer.

* * * * *